(12) United States Patent
Kayan et al.

(10) Patent No.: US 6,330,964 B1
(45) Date of Patent: Dec. 18, 2001

(54) APPARATUS AND METHOD FOR SURGICAL FASTENING

(75) Inventors: Helmut L. Kayan, Redwood; James E. Jervis, Atherton, both of CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

(21) Appl. No.: 09/285,478

(22) Filed: Apr. 2, 1999

Related U.S. Application Data

(63) Continuation-in-part of application No. 09/113,827, filed on Jul. 10, 1998, now Pat. No. 6,228,098.

(51) Int. Cl.$^7$ ................................................. A61B 17/068
(52) U.S. Cl. .......................................... 227/176.1; 227/19
(58) Field of Search ............................... 227/175.1, 176.1, 227/82, 19

(56) References Cited

U.S. PATENT DOCUMENTS

| | | |
|---|---|---|
| 4,895,289 | 1/1990 | Richards et al. . |
| 5,246,156 | * 9/1993 | Rothfuss et al. ................... 227/176.1 |
| 5,356,064 | * 10/1994 | Green et al. ............................ 227/19 |
| 5,372,600 | 12/1994 | Beyar et al. .......................... 606/106 |
| 5,381,943 | * 1/1995 | Allen et al. .............................. 227/19 |
| 5,425,489 | * 6/1995 | Shichman et al. ................. 227/175.1 |
| 5,544,802 | * 8/1996 | Crainich ............................. 227/176.1 |
| 5,816,471 | 10/1998 | Plyley et al. .......................... 227/176 |
| 5,817,109 | 10/1998 | McGarry et al. ..................... 606/143 |

FOREIGN PATENT DOCUMENTS

| | | |
|---|---|---|
| 0 168 244 | 1/1986 | (EP) . |
| 0 570 087 | 11/1993 | (EP) . |
| WO 00/02490 | 1/2000 | (WO) . |

* cited by examiner

Primary Examiner—Scott A. Smith

(57) ABSTRACT

Apparatus for applying fasteners during endoscopic surgery includes a handle portion, a triggering mechanism and a fastener application. The fastener applicator is detachable from the handle portion by virtue of a rotational locking system and may be replaced with a new fastener applicator having a fresh load of vertically stacked fasteners. The fastener may be formed around a single point on an anvil. The fastener applicator having only one actuated part in its applicator mechanism, and makes use of biased springs controlled by the position of the actuated part for the remaining part of the mechanism. Another embodiment of the invention deploys a plunger/ratchet assembly and pawl within the handle portion of the apparatus to ensure that the apparatus applicator mechanism will not reverse in the middle of a triggered application stroke. A method of applying a fastener includes the following steps: moving a fastener from a storage channel, where it has been vertically stacked, to a driving channel by a biased fastener positioning spring as a slide is retracted; advancing the slide until the slide engages the fastener in the driving channel and drives the fastener over an anvil to form the fastener. During advancement of the slide a biased stop spring is forced back into a recess thereby allowing the next fastener to move forward in the storage channel in response to the force of a biased pusher spring; retracting the slide thereby freeing the biased ejector springs to kick the formed fastener off the end of the anvil; and further retracting the slide until the fastener positioning spring is once again free to move the distal-most fastener from the storage channel into the driving channel.

5 Claims, 22 Drawing Sheets

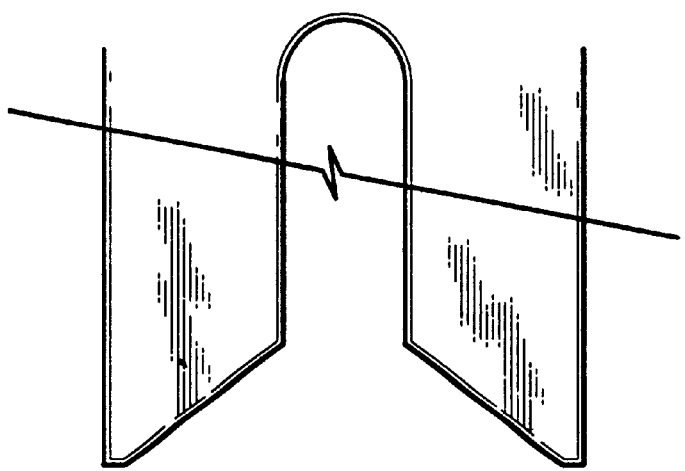
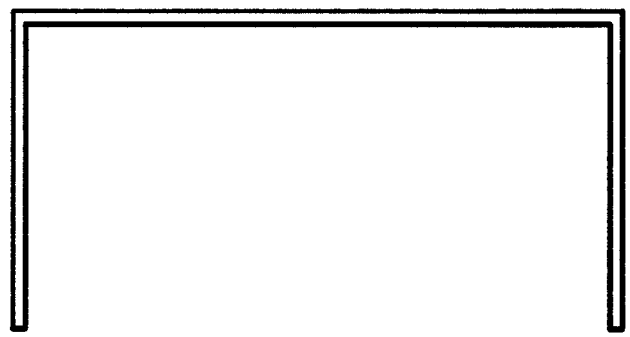
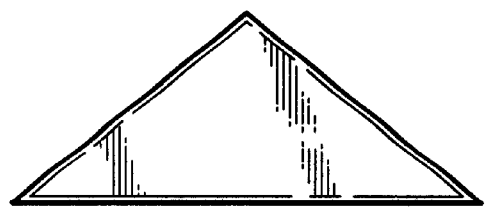
FIG. 1

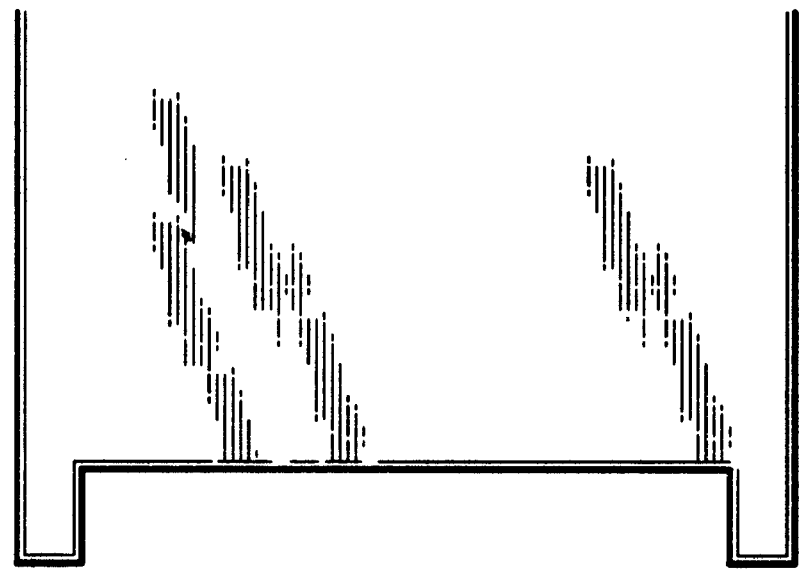
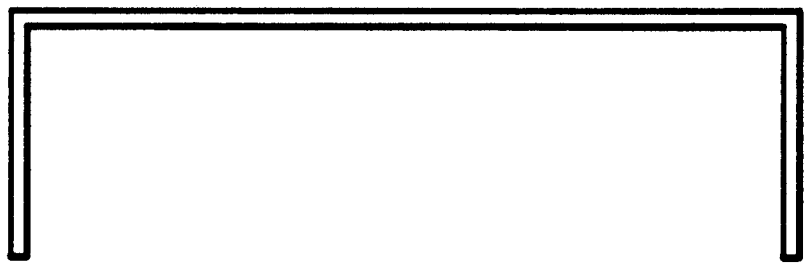
FIG. 2

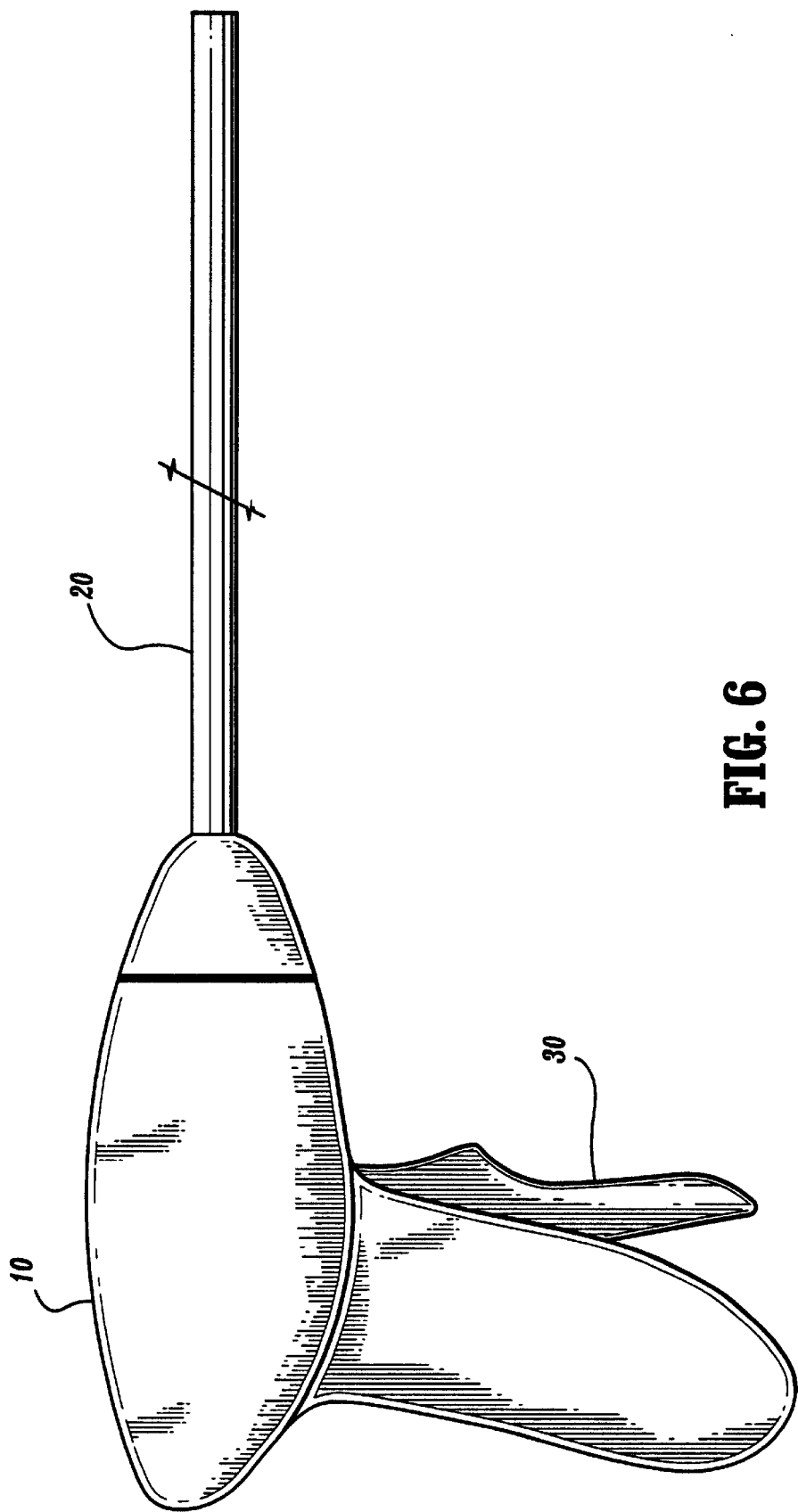

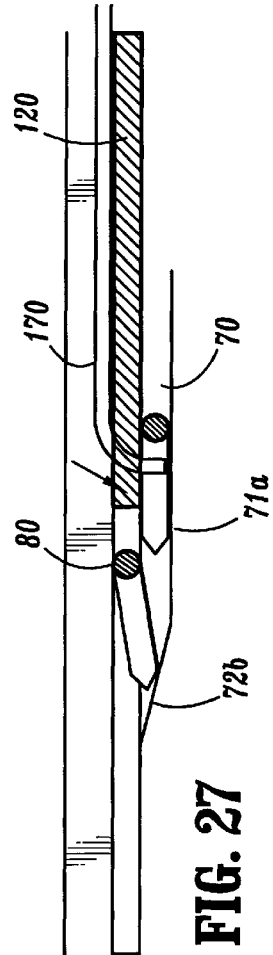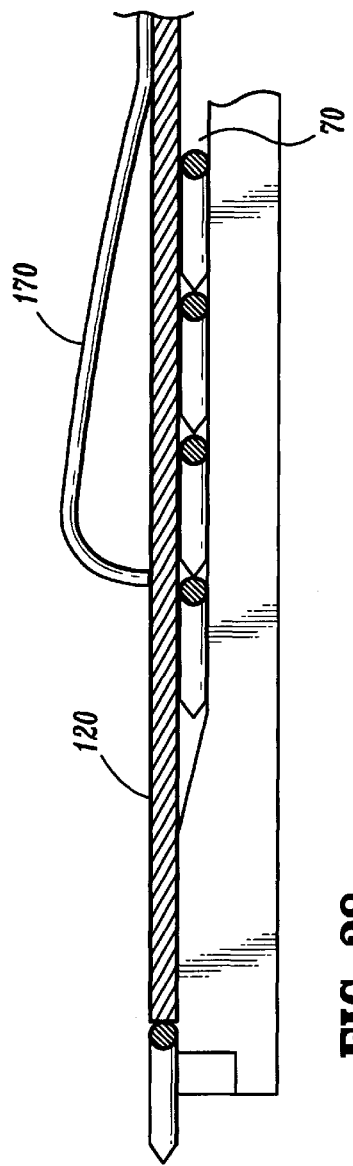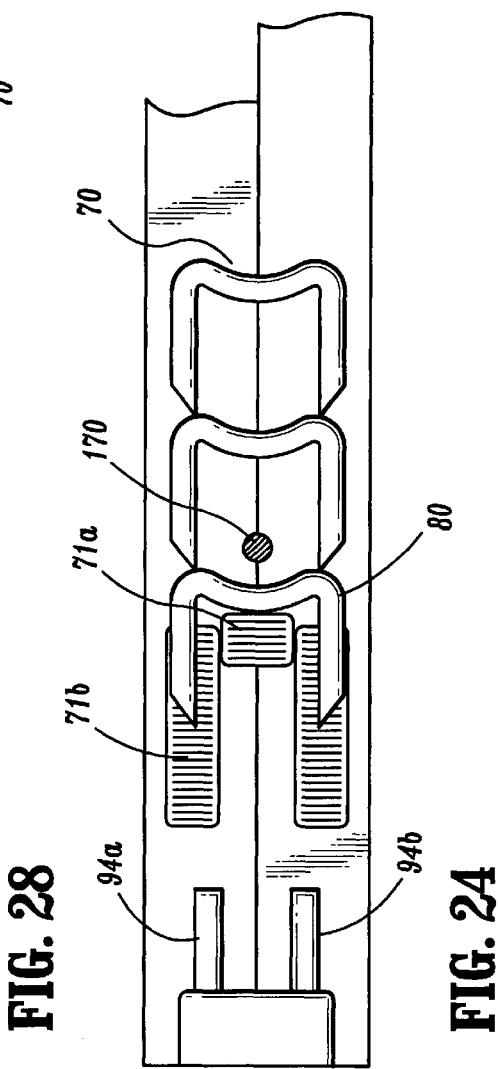

APPARATUS AND METHOD FOR SURGICAL FASTENING

The present application is a continuation-in-part of U.S. application Ser. No. 09/113,827 filed on Jul. 10, 1998, now U.S. Pat. No. 6,228,098.

FIELD OF THE INVENTION

The present invention relates generally to surgical fastening tools for fixating tissue and/or surgical materials during minimally invasive surgery, and particularly to a surgical fastening tool having a space-efficient, simplified fastening mechanism that permits deployment of the tool through a minimal opening but which also maximizes the gripping area of the applied surgical fastener. More particularly, the invention relates to a reduced diameter (5 mm) surgical fastening tool for use in hernia repair. The tool is deployed through a reduced diameter access port in the body to fasten a piece of surgical mesh to body tissue using a specially formed fastener having a maximized gripping area. The tool also has a simplified, jam-free fastening mechanism. The present invention also relates to methods for repairing a patient's hernia through a minimized diameter access port while maximizing the gripping area of the surgical fastener as well as methods for applying surgical fasteners from a miniatured device with reduced risk of jamming.

BACKGROUND OF THE INVENTION

During some surgical procedures, most notably hernia repair procedures, it is considered desirable by many practitioners to reinforce the muscle tear or other defect with a piece of surgically implantable mesh. Physicians most often use an open-weave, sintered mesh made of polypropylene and hold it in place by a type of permanent fixation method. One common method of fixation uses metallic fasteners, such as staples, which remain in the body permanently after the hernia repair. Medical device designers have created a number of larger size devices to fasten tissue and/or surgical materials to tissue during minimally invasive surgery. According to these designs, the devices typically contemplate a 10 -mm or wider application tool used to deploy a fastener. For example, Green et al., U.S. Pat. No. 5,356,064, col. 21,II. 34–53, describes a device for deployment through a 12 mm trocar guide tube wherein the device stacks a set of staples at roughly a forty-five degree angle to the axis of the device to provide greater visibility. See Green et al. FIG. 18.

However, these tools are being judged too large for deployment according to the current minimally invasive techniques which are bringing the size of the surgical instruments and access ports down to a 5 mm diameter. Moreover, Green et al. cannot be readily scaled down because of physical limitations caused by the generally transverse stacking of fasteners. See Green et al., FIG. 18. In addition, the design of Green et al. cannot be effectively scaled down because the fastener discharged by the application tool must be of sufficient scale to securely span across the defect and/or strands of surgical mesh and efficaciously engage sufficient tissue area for adequate gripping strength. Green et al. employs a fastener forming system which unduly reduces the finished span or width of the fastener relative to its initial width. See Green et al., FIGS. 20–21, col. 22,II. 38–48. Thus, reduction in Green et al.'s tool diameter would result in an unsatisfactory gripping area for the finished fastener.

In addition to reducing fastener-gripping strength, smaller diameter tools have other problems. For example, miniaturization of the surgical fastening tool increases the likelihood of jamming, a common problem for minimally invasive surgical fastener tools, because the critical tolerances for the device's moving parts would be reduced along with the size of the instrument. Accordingly, slight changes in deployment stress and temperature can effect the mobility of the moving tool parts. The Origin Tacker, though of 5 mm diameter, employs a rotational actuation mechanism to deploy a helical fastener. Rotation increases the complexity needed for the actuation mechanism, and creates greater need to ensure reliable translation of trigger action.

What is needed is a space-efficient surgical fastening tool that minimizes its outer diameter while maximizing the gripping area and strength of the fastener. The fastening mechanism of the desired surgical fastening tool must not be complicated and should be limited to a few actuated parts to reduce the probability of jamming during minimally invasive surgery. The device should be designed to avoid double firing and incomplete firing. The device should also permit for the easy reloading of additional fasteners during extensive surgical procedures. The prior art devices are inadequate to meet these objectives.

SUMMARY OF THE INVENTION

The present invention relates to surgical fasteners, fastening tools and methods for securing tissue and/or surgical materials during minimally invasive surgery. In particular, the devices of the present invention are adapted to minimize the diameter of the surgical fastening tool while maximizing the area gripped by the fastener. Furthermore, the devices of the present invention are adapted to discharge the fastener by way of a simplified fastening mechanism with few actuated parts. The surgical materials to be fastened may be surgical mesh, sutures, prostheses, linings or the like. The tissue to be fastened may be tissue, foreign or endogenous to the patient.

In one embodiment, the apparatus includes three major elements: a fastener applicator comprising a fastener magazine; a handle portion to which the applicator is attached; and a triggering mechanism. The triggering mechanism may be housed in either the fastener applicator, the handle portion or in a combination of the two. In a first aspect of the invention, the fastener applicator has a cantilevered anvil with a cross section around which the fastener may be formed at a single focal point when the fastener is pressed by a slide. The fastener may initially be M-shaped, upside-down U-shaped or other suitable shape. In a most preferred embodiment, the anvil has a cross section that is essentially triangular and a shaping slide with a cooperating notch that is angled to closely receive the triangular cross-section of the anvil. FIG. 1. Importantly, according to this first aspect of the invention, the single-point anvil permits the width of the slide which forms the fastener to be the same or less than the width of the stored fastener but without sacrificing the finished span (installed width) of the applied fastener and the area it encloses. An anvil with a semi-circular or other round edged cross-section may also be used in combination with a round-notched slide. The space-efficiency of the slide and anvil permits a reduction in the overall width of the fastener applicator relative to the width of the fastener. Traditional staple type surgical fasteners have a slide which, when of reduced width, unacceptably reduce the span of the applied fastener to accommodate the "horns" of the slide. See FIG. 2.

In one embodiment, the apparatus is of unitary, non-detachable design wherein a fastener applicator, handle portion and a triggering mechanism are provided in a single integral unit. The fasteners may be stored in the handle portion of the apparatus or loaded from outside the device just prior to use. However, according to a second aspect of the invention, the applicator functions as a fastener magazine and is readily removed from or locked onto the handle portion by virtue of a novel mechanism for quick attachment and detachment. The applicator comprises a slide actuator which operates a slide in response to operation of the triggering mechanism to discharge fasteners. The novel mechanism locks the slide actuator into a secure, locked position within the detached applicator magazine so that the slide actuator is properly located to engage the motion-translating parts of the triggering mechanism of the device when attached. The novel mechanism then automatically frees the slide actuator upon attachment of the applicator to the handle thereby making the device ready for use. Specifically, the novel mechanism employs an "L-shaped" pin with a recessed region that rotates into and out of engagement with the slide actuator based on its interaction with pre-formed recesses in the handle of the device during attachment and detachment. Thus, according to a preferred embodiment employing this second aspect, when the applicator comprising a magazine of fasteners runs out of fasteners, the user may substitute a second applicator containing a fresh magazine. This construction also permits the handle portion to be sterilized and re-used.

The fastener applicator may either be of unitary construction or made of several interconnecting pieces. However, in the preferred embodiment, a tube of circular cross-section houses a magazine formed by the juxtaposition of two cooperating half shells, known collectively as the insert, each half-shell having essentially a semi-circular cross section. The two-half shells are preferably inserted into the tube during manufacture. When combined, the two half-shells and the slide form the magazine or storage channel which contains a set of vertically stacked fasteners. The fastener applicator is separable from the handle portion so that the handle portion may be supplied with a new applicator containing a new set of fasteners once the first set of fasteners has been used.

A third aspect of the invention minimizes the possibility of jamming caused by an improperly timed interplay between independently moving parts and also reduces the probability of jamming due to the failure of the trigger to actuate a key part of a multi-part actuation mechanism. Thus, in the preferred embodiment of the device employing the third aspect of the invention, the insert and slide form two channels: a fastener storage channel and a fastener driving channel. The fastener storage channel contains a plurality of vertically stacked fasteners, stacked tips to back, thereby reducing applicator width relative to tools which use transversely stacked fasteners. The fasteners are continually urged toward the distal end of the applicator by a pusher that is biased by a pusher spring. The fastener-driving channel further houses a slide that rides in the driving channel to engage the back of the first fastener positioned within the driving channel. According to the most preferred embodiment, movement of the slide drives the fastener onto the anvil while the notch in the slide shapes the fastener over the anvil according to the first aspect of the invention.

In the preferred embodiment, the insert additionally comprises a system of leaf springs that assist in securely positioning and advancing the fasteners one at a time during the repeated fastener application process. The action of the leaf springs is controlled by slide location. Accordingly, in the most preferred embodiment of the third aspect, the applicator contains one actuated part, the slide, that is moved by the active application of force generated by the triggering mechanism. The rest of the moving parts in the applicator are biased to move in a certain direction but are restrained or liberated based on the location of the slide.

According to this most preferred embodiment, with the applicator held against the target, the slide is fully advanced distally to drive the first fastener's tips into the target and to shape the fastener on the anvil. When the slide is subsequently retracted after shaping the first fastener, a pair of biased ejector springs are liberated and kick the formed fastener off the end of the anvil, freeing the apparatus from the fastener. Upon further retraction of the slide, a biased fastener positioning spring is released and pushes the second fastener from the distal most position in the storage channel into the driving channel. Meanwhile, a biased stop spring restrains the third fastener from advancing in the storage channel until the second fastener is being advanced in the driving channel. The third fastener is then released by the depressed stop spring and advanced to the distal most position in the storage channel. Fully actuating the slide to discharge the second fastener and then fully retracting the slide positions the third fastener in the driving channel. This process may be repeated until each of the fasteners in the magazine has been applied.

In the interest of further reducing the potential for jamming of the miniaturized tool during surgery, according to a fourth aspect of the invention, the apparatus may employ a unique jam-free ratchet and pawl mechanism, housed in the handle portion, that assures complete travel of the slide in both directions during application of each fastener. This embodiment of the apparatus comprises a plunger assembly that is linked to the slide by means of the slide actuator. Complete forward and reverse movement of the plunger assembly results in a complete corresponding motion of the slide. In the preferred embodiment, the plunger assembly reciprocates forward and backward within the body of the handle portion. The body of the handle has a tapered slot, adjacent to the plunger assembly, which contains a pawl. The side of the plunger assembly that is immediately adjacent to the tapered slot contains a series of grooves which collectively form a ratchet extending for a distance approximately equal to the travel of the plunger assembly. The length of the pawl is longer than the perpendicular distance from the bottom of the tapered slot to the bottom of the ratchet grooves, such that once the pawl is engaged in the ratchet grooves, the pawl is oblique and prevents reversal of the plunger's direction of travel.

When the pawl has moved past the end of the ratchet, a wire spring urges the pawl to assume a position transverse to the direction of travel. As the plunger assembly is moved back towards its original position, the pawl again engages the ratchet but with opposite orientation. Accordingly, the pawl again prevents reverse travel of the plunger assembly until the stroke is fully completed and the pawl has cleared the length of the ratchet. The spring then reorients the pawl transversely in preparation for the next stroke. In this way, the invention prevents the slide, which is connected to the plunger assembly by the slide actuator, from reversing mid-stroke and safeguards against jamming, non-firing and misfiring.

The methods of the present invention relate to deploying a fastener with maximized gripping area using a space-efficient deployment mechanism having few actuated parts. In a preferred method of the invention, a hernia repair patient is incised and fitted with a port to access the site of the hernia. After access to the site of the hernia is achieved, the hernia is reduced and the surgical mesh is placed over the defect using minimally invasive techniques. The surgical fastening tool apparatus is deployed through an access port and its tip pressed against the mesh and the tissue to be fastened. The tool is then triggered by means of the triggering mechanism. The fastener is then formed by the action of the slide pressing the fastener onto the surface of the anvil. In this manner, the mesh is secured to the body tissue by the gripping strength of the fastener.

When employing the first aspect of the invention, the method of the present invention generally includes the following steps: forming a fastener by placing it over a single focal point anvil; pressing the fastener against the single focal point anvil using a slide having a width that is approximately the same as or less than the width of the fastener; discharging the fastener into the tissue of the patient.

In a method that employs the second aspect of the invention, the method of fastener application is executed within a detachable applicator which may be readily replaced with a second applicator containing additional fasteners using a novel mechanism.

In a method that employs the third aspect of the invention, a fastener is applied by the following preferred steps: the fastener is moved from the storage channel where it has been vertically stacked to the driving channel by the biased fastener positioning spring as the slide is retracted; the slide is then advanced until the slide engages the fastener in the driving channel and drives the fastener over the anvil to form the fastener. During advancement of the slide the biased stop spring is forced back into a recess in the insert thereby allowing the next fastener to move forward in the storage channel in response to the force of the biased pusher spring; the slide is then retracted, freeing the biased ejector springs to kick the formed fastener off the end of the anvil; finally the slide is further retracted until the fastener positioning spring is once again is free to move the distal-most fastener from the storage channel into the driving channel.

The present invention was developed, in part, out of recognition of the need for a reduced diameter fastening tool which could discharge, from a reduced diameter applicator, a fastener that firmly holds mesh and tissue together. Unlike a traditional staple shape where the back of the staple lies parallel to the tissue surface into which it is deployed, the present invention teaches that a U-form wire fastener applied in the form of a diamond relative to the tissue surface has certain advantages including reduction in the size of fastener needed to achieve high gripping strength. The installed span of the fastener and the area captured by the fastener are two useful parameters for evaluating the efficacy of a fastener. FIGS. 3a and 3b on Table 1 demonstrate the conventional finishing of a "U" shaped staple by assuming an arbitrary initial width of 8 mm (assuming negligible thickness of the wire and bends of 90 degrees) and monitoring these two parameters. The traditional "U"-shaped staple may have many finished shapes depending on the width selected between bends in the back of the staple. In essence, the width between bends determines the finished span of the applied staple. See FIG. 3b. The length of the staple legs is arbitrary but the legs should not reach too deeply into the tissue to avoid damaging underlying structures. On the other hand, the staple must reach deeply enough to enclose sufficient tissue to develop adequate holding strength.

With reference to FIG. 3b and Table 1, it is clear that, as the finished conventional staple span is stepwise decreased, the area of the projected rectangle formed by the finished staple goes through a maximum value (8). By comparison, the invention's preferred diamond shaped fastener, described in FIGS. 4b and Table 2, has a finished span of .707 × the initial width, W, and encloses a projected area double the size of the maximum traditional design (16). Moreover, the preferred diamond-shaped finished fastener shown in FIG. 4b, maintains a span greater than all but the most extreme of possible finished shapes made by the conventional process (shapes which suffer from greatly diminished gripping area). Although the user may choose other initial widths as well as other bend angles for the traditional method, the relative relationship between the gripping area of the diamond fastener of the present invention and the conventional finished fastener remain. When viewed in light of the longer finished span permitted by the present invention, these Figures and Tables demonstrate the superior geometry of the finished fastener formed by the instant apparatus.

TABLE 1

CONVENTIONAL DESIGN
W − 2L = SPAN
L × SPAN = AREA

| W | 2L | SPAN | AREA |
|---|----|------|------|
| 8 | 2  | 6    | 6    |
| 8 | 3  | 5    | 7 ½  |
| 8 | 4  | 4    | 8    |
| 8 | 5  | 3    | 7 ½  |

TABLE 2

FASTENER FORMED BY PREFFERED EMBODIMENT OF THE INVENTION $$\frac{\left(\frac{W}{2}\right)}{\left(\frac{Span}{2}\right)} = \frac{\sqrt{2}}{1}$$

$$SPAN = \frac{1}{\sqrt{2}} W = 0.707\ W$$

$$AREA = \left(\frac{W}{2}\right)^2$$

Thus, if W = 8, SPAN = 5.66
AREA = 16

To the extent the finished angle of the inserted legs relative to the surface plane of the tissue is related to the fastener's strength, a fastener's legs which finish parallel to the tissue surface are superior to those which finish perpendicular to tissue. Accordingly, in an alternate embodiment, described in FIGS. 5a and 5b and Table 3, the fastener may be initially formed with an upwardly concave back of an arbitrary angle and with legs which are initially parallel, approximating the capital letter "M". FIG. 5a. In the embodiment shown, the angle of the concave back is greater than ninety-degrees. During formation of the fastener the central bend is reversed to allow the legs to finish more parallel to the tissue surface. FIG. 5b. According to this embodiment, the length of the finished span remains essentially the same as the finished span shown in FIGS. 4a, 4b but the projected area gripped by the fastener is reduced.

TABLE 3

SPAN ≦ .707W
AREA = ½(>W/2)² ≧ 8

The gripping area is reduced to a value that is still greater than or equal to the maximum area gripped by the conventionally processed U-shaped design described in FIG. 3b. Importantly, the finished span of the conventionally processed U-shaped design is substantially less (.5W=4) compared to the finished span of the concave back fastener (.707W=5.66). Thus, it is clear that with respect to the length of the finished span and the gripping area of the fastener, triangular finished fastener designs, shown in FIG. 5b, are also superior to conventionally processed designs. This recognition is particularly important when the goal is to miniaturize a surgical fastening tool for use in minimally invasive surgery.

Miniaturization of a fastener tool places a premium on the gripping efficiency of the fastener relative to the space available for its deployment within the small diameter of the applicator. Assuming that the applicator of a surgical fastening tool comprises a tubular housing, a slide that forms the U-shaped fastener with two bends in the back must have "horns" and be wider than the finished span thereby wasting tool diameter.

Thus, as a practical matter, the conventional mechanism necessarily results in a fastener with a smaller finished span for a given tool diameter. See FIG. 2. In contrast, the finished diamond and triangular fasteners shown in FIGS. 1, 4b and 5b, do not need the slide to be wider than the finished span of the fastener.

Using the fastener and anvil configurations of FIGS. 4 and 5, the tool design need not sacrifice the length of the finished span to accommodate the fastener forming apparatus itself. Moreover, the disclosed invention requires less force to deploy the fastener because only one bend is formed during deployment rather than two bends as with the conventional design. This reduction in force is a significant advantage for a miniaturized device whose miniaturized parts are relatively weak and may fail under repeated stress.

The present invention was also developed in part to solve other problems associated with miniaturization of fastener devices, such as jamming, non-firing and misfiring. Thus, the invention contemplates that the deployment mechanism of the device has few mechanically actuated parts because the critical tolerances for such actuated parts are reduced in the miniaturization process. Moreover, surgical fastening tools are at times roughly handled in a hospital setting and may undergo significant abuse during sterilization. This can cause the internal uncoupling of actuated parts or other damage not visible from the surface of the tool, only to be discovered during use of the device. Thus, a feature limiting the number of actuated parts leads to a sturdier, more reliable device. This feature also simplifies the manufacturing process.

Some users may also wish to maximize the finished span of the fastener. For example, in a variation on the triangular design of FIG. 5b, the fastener would begin as an "M" such as in FIG. 5a but finish as an inverted triangle, the top end lying substantially flat against the fastened tissue or mesh with the legs bent to essentially form a triangle as shown in FIG. 5c. In this way, finished span is maximized. This result can be accomplished by limiting travel of the slide so as to stop short of complete forward compression against the anvil.

The finished span may be further maximized, as shown in FIGS. 20a and 20b and FIGS. 21a and 21b. One way of doing this involves deploying two anvils attached to the applicator tube rather than a single anvil. FIG. 22 depicts a two-anvil system with slide forming the finished fastener of FIG. 20b. Similarly, FIG. 23 depicts the same two anvil system with slide forming the finished fastener of FIG. 21b by virtue of a reduction in the forward travel of the slide. The two anvils 131 have an essentially half-circular cross-section. The slide/anvil combination shown in FIGS. 22 and 23 is effectively a mechanical inversion of that used to produce FIG. 3b and FIG. 4b. The ultra wide finished span of the fastener disclosed in FIGS. 20b and 21b may eliminate undesirable pinching of nerves in areas with dense or unforeseen nerve tissue.

The invention was also motivated by the knowledge that miniaturization of the surgical fastening tool may cause the tool to carry fewer fasteners than may be needed for a particular surgical procedure. Thus, according to another aspect of the invention, the fastening tool comprises an interchangeable fastener magazine.

It is a general object of the present invention to eliminate or reduce the problems associated with jamming of small diameter surgical fastening tools.

It is another object of the present invention to reduce the number of actuated parts in the deployment mechanism of the tool so as to reduce the number of critical tolerances between coupled parts and reduce the risk of decoupling or other malfunction. For example, in one embodiment of the invention, the insert of the fastener applicator incorporates only one actuated component.

Another object of the present invention is to maximize the gripping area of the fastener while reducing the diameter of the applicator of the surgical fastening tool. Because of the nature of surgical repair, it is undesirable to have to refasten the surgical material after surgery is completed. Accordingly, the fasteners should form a strong link between the fastened materials and/or tissue so that the materials stay in place during post-surgical patient activity. Secure fasteners have previously required larger diameter fastening tools which are incompatible with the new, reduced-diameter, minimally invasive surgery techniques.

It is a further object of the invention to provide a surgical fastening tool that is economical and convenient for fastening hernia mesh and the like during minimally invasive surgery.

It is a further object of the invention to provide a surgical fastening tool with an interchangeable magazine portion that permits fast and reliable introduction of new fasteners into the tool.

It is further object of the invention to provide a disposable, detachable applicator which contains a complete fastening mechanism and set of fasteners, thereby permitting both the fast, convenient replacement of fasteners during surgery as well as the reuse of the handle and trigger portions.

It is a further object of the invention to ensure complete travel of the tool's fastening mechanism in each direction to prevent against partial firing, empty firing and jamming during use.

As for the methods of the invention, one object of the invention is to provide a fastening mechanism that is both compatible with minimally invasive surgery techniques using reduced port diameters (5 mm is the newest standard in the field of minimally invasive surgery) and which provides fasteners that maximally grip the area of tissue and material.

It is a further object of the invention to provide a method of applying a fastener during minimally invasive surgery that includes easy replacement of spent fastener magazines.

It is a further object of the invention to provide a reliable method for fastener application during minimally invasive surgery that avoids jamming, non-firing and misfiring.

BRIEF DESCRIPTION OF THE DRAWINGS

Reference is made to a brief description of the drawings, which are intended to illustrate surgical fastening tools for use herein. The drawings and detailed description which follow are intended to be merely illustrative and are not intended to limit the scope of the invention as set forth in the appended claims.

FIG. 1 is a schematic front view of an embodiment of the preferred fastener, space-efficient shaping slide and anvil of the present invention.

FIG. 2 is a schematic front view of a traditional staple with its shape-forming slide about to form the staple on a rectangular anvil.

FIG. 6 is a longitudinal view of one embodiment of the surgical fastening tool that includes a handle portion, a trigger portion and an applicator.

FIG. 24 is a schematic top view of the storage channel of an alternate embodiment of the first half-shell of the fastener applicator.

FIG. 27 is a cut-away side view of the alternative embodiment of the fastener applicator with the slide in the retracted position.

FIG. 28 is a cut-away side view of the alternative embodiment of the fastener applicator with the slide fully extended.

DETAILED DESCRIPTION OF THE INVENTION

Figure 7:
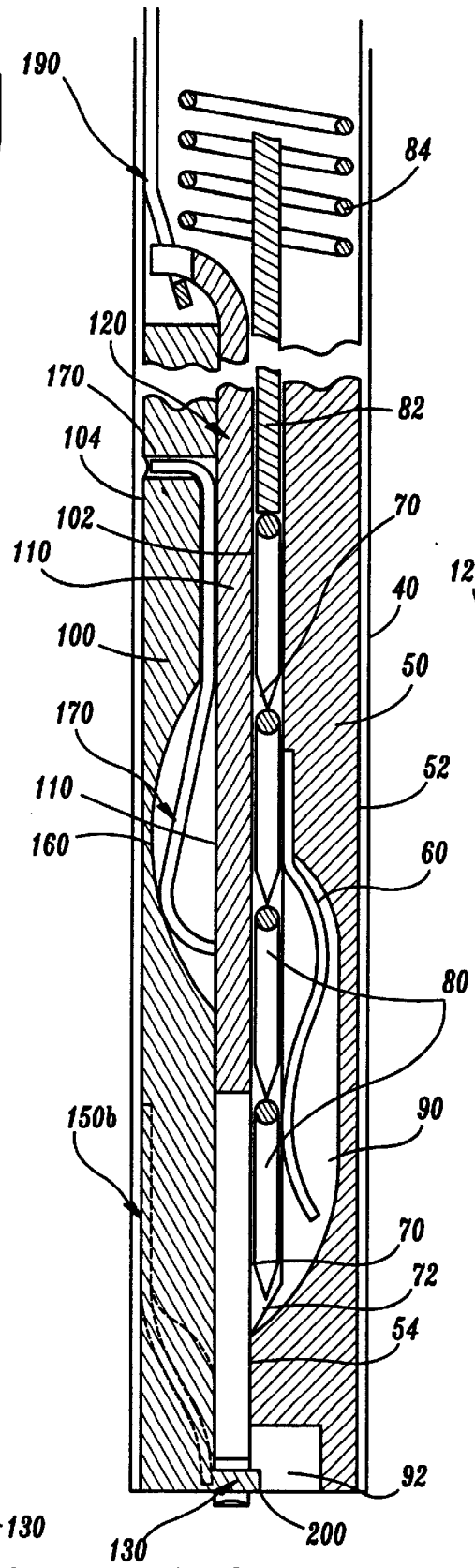
FIG. 7 is a cross-section of the applicator of one embodiment of the surgical fastening tool with the slide fully extended distally.

Referring more particularly to the drawings, FIG. 6 shows one embodiment of the surgical fastening tool. The surgical fastening tool comprises a handle portion 10 an applicator 20 and a trigger portion 30. FIG. 7 shows a cut-away cross-section of a preferred embodiment of the applicator portion of the device. According to the preferred embodiment, the applicator comprises a tubular housing 40 having an insert contained within. Although the insert could be made as a single unit or even be manufactured out of a single piece that forms the tubular housing, the insert is preferably made from two cooperating half-shells which are inserted into the tubular housing. The half-shells preferably have a beveled outer edge which permits crimping of the distal most end of the tubular housing to secure the insert. In the preferred embodiment, the first half-shell 50 has a rounded side 52 which abuts the tubular housing 40 and a flat side 54 that has recessed region 70 whose surface forms one the walls of the fastener storage channel containing fasteners 80. Above the fasteners 80 sits a pusher 82, which rides in the fastener storage channel. The pusher 82 continuously exerts a downward pressure on the vertically stacked fasteners 80 by virtue of a biased pusher spring 84.

Recessed region 70 gradually rises to the diametrical plane of flat side 54 (diametrical relative to the tube circumference on flat side 54) by virtue of a slanted ramp 72. A fastener positioning spring 60 attached to and flush with the recessed portion 70 of flat side 54 of the first half-shell 50 is biased to extend beyond both the recessed region 70 of the flat side 54 and the most prominent plane of the flat side 54. The spring 60 is capable of being completely contained within a slot 90 in the first half-shell. Finally, the first half-shell 50 has a cut-away region 92 at the distal end of the applicator to permit ejection of the fastener.

Figure 9:
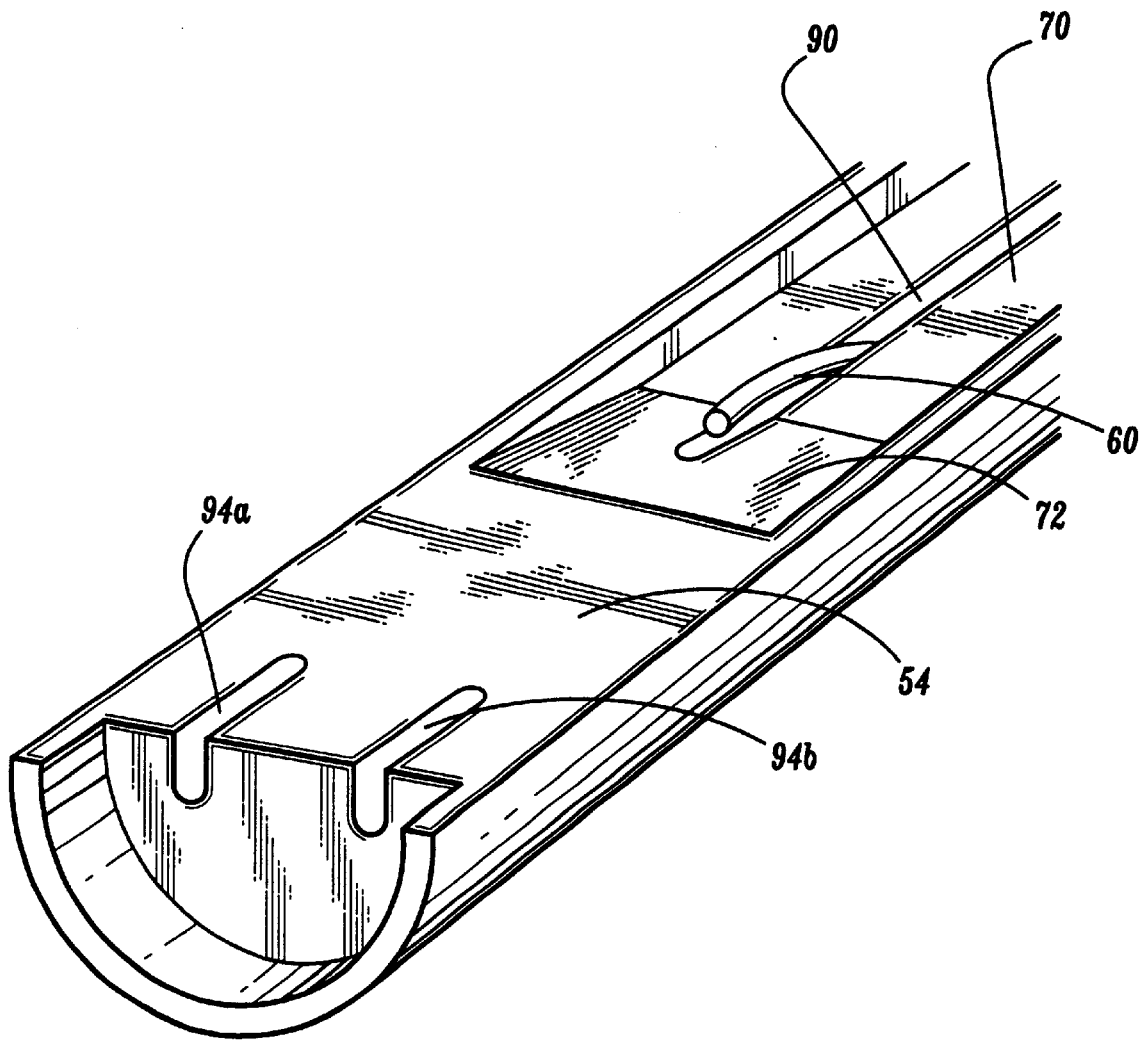
FIG. 9 is a three-dimensional rendering of the first half-shell and fastener positioning spring of the applicator shown in cross-sectional perspective in FIGS. 7 and 8.

A perspective view of the first half-shell 50 is shown in FIG. 9. The diametrical plane of flat side 54 appears uppermost in the drawing. This view shows that in a preferred embodiment the cut-away region 92 has two further recessed regions 94a and 94b.

Figure 10:
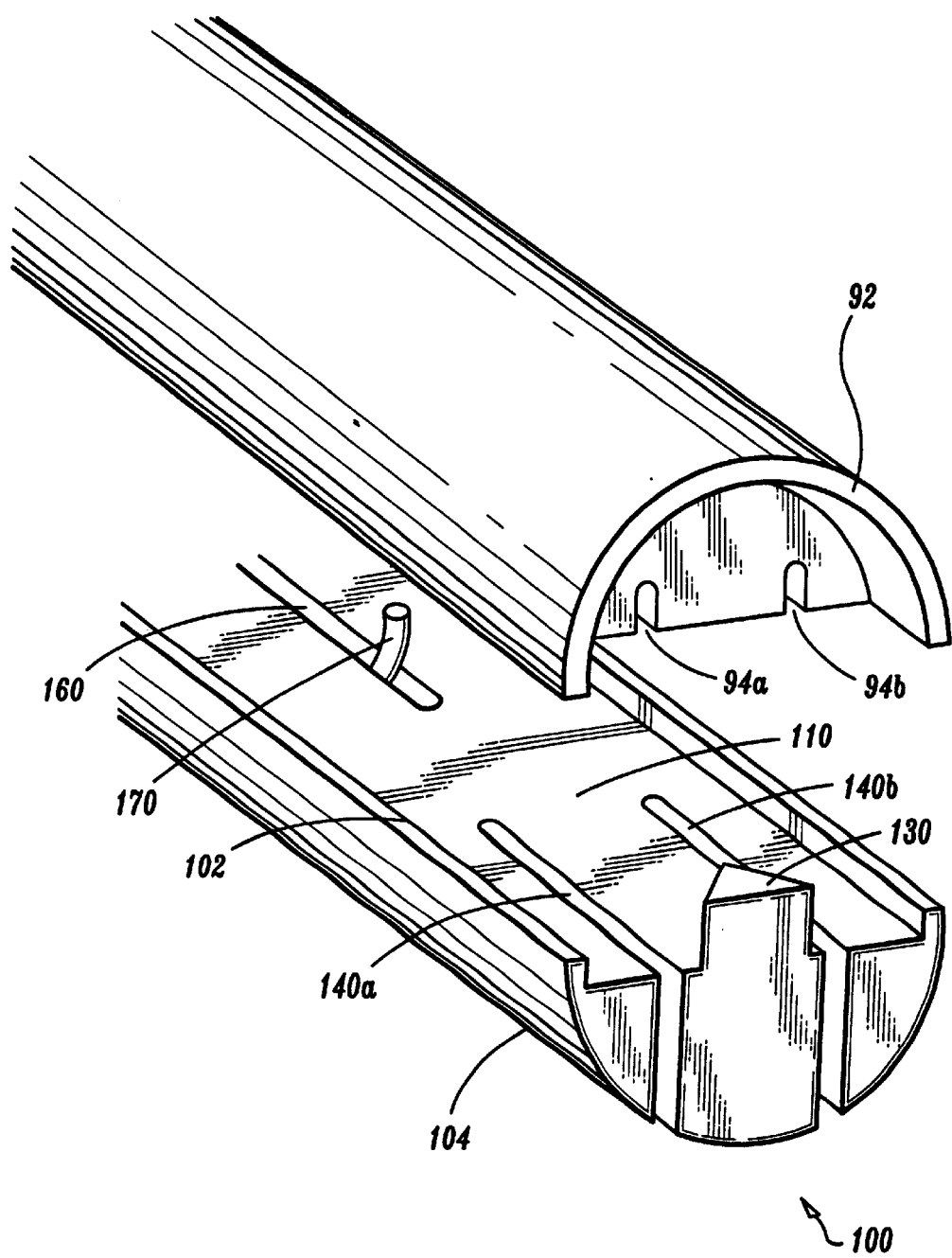
FIG. 10 is a three-dimensional rendering of the second half-shell of the applicator and stop spring shown in cross-sectional perspective in FIGS. 7 and 8, with the first half shell poised above.
Figure 12A:
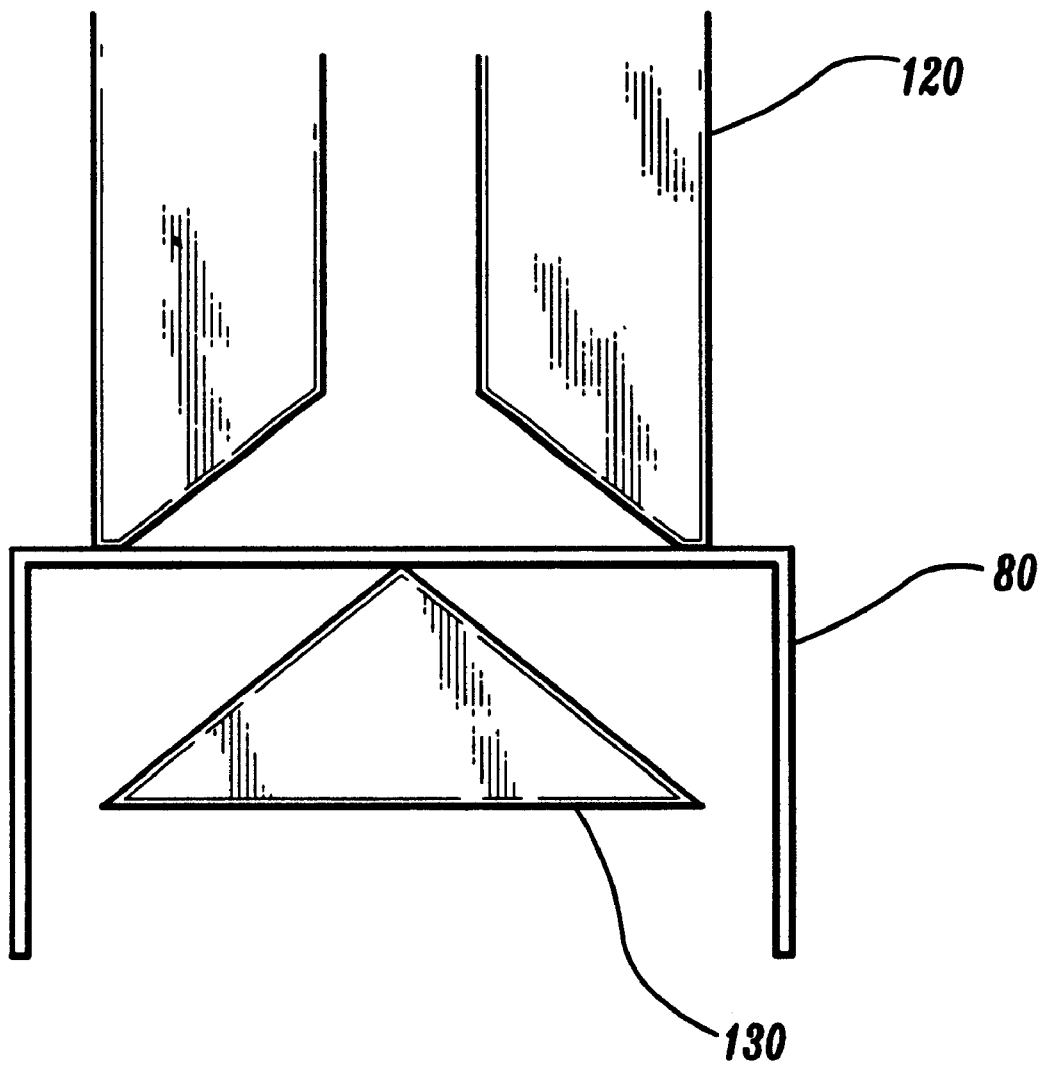
FIG. 12a is a schematic front view of the preferred slide and fastener of the present invention prior to forming of the fastener.
Figure 12B:
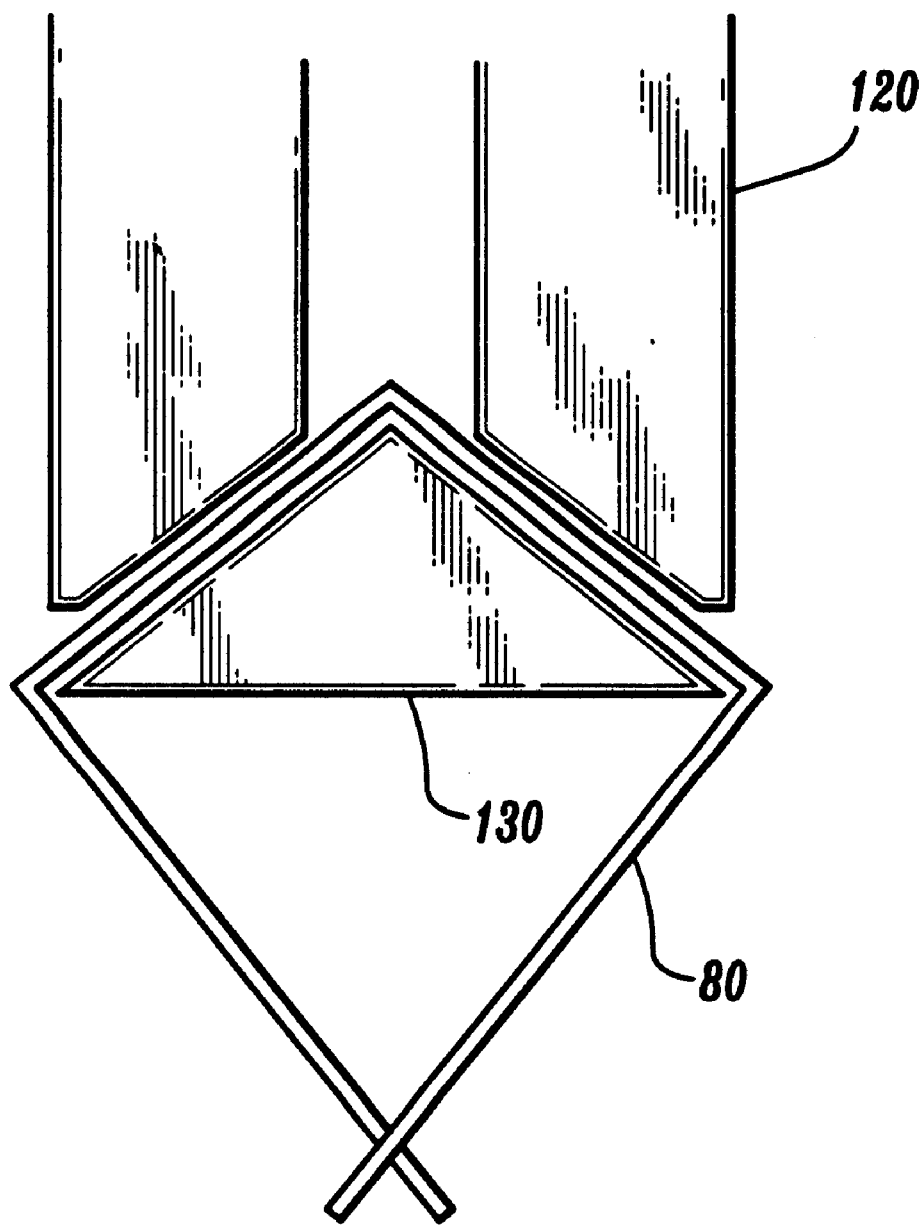
FIG. 12b is a schematic front view of the preferred slide and fastener of the present invention after the forming of the fastener.
Figure 12C:
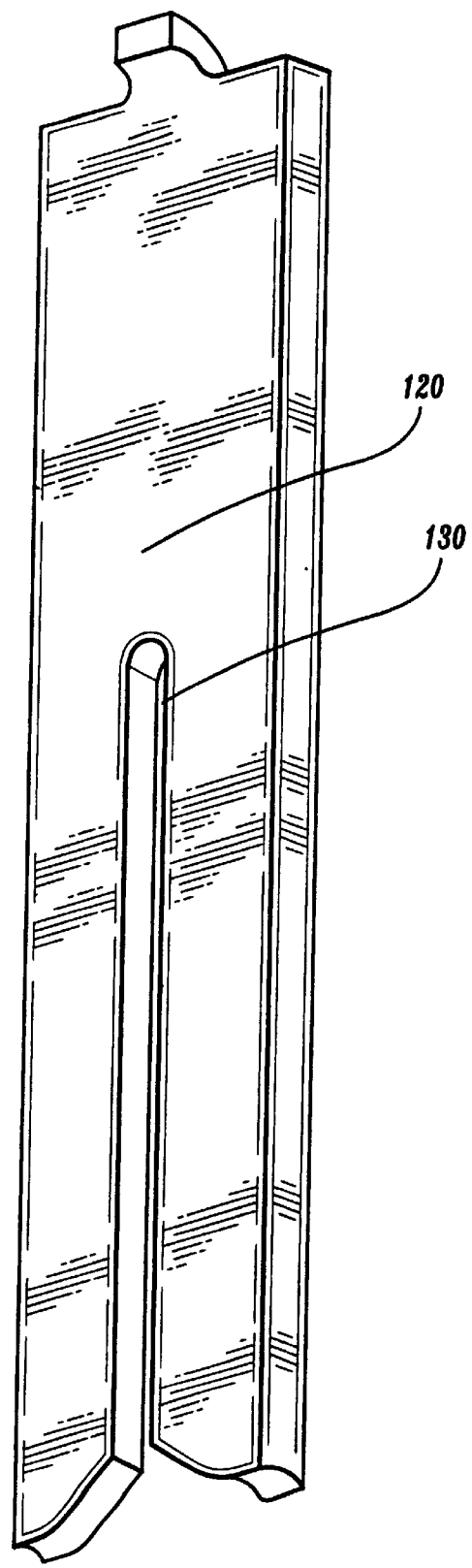
FIG. 12c is a three-dimensional rendering of the preferred slide of the present invention.

A second half-shell 100, shown in FIG. 10, has a flat side 102 and a rounded side 104. Flat side 102 has a recessed area 110 whose plane forms one of the walls of the driving channel in which slide 120 rides. The distal end of second half-shell 100 comprises an anvil 130 with a triangular cross-section. Anvil 130 is a cantilever that extends beyond the recessed area 110 across the driving channel and into cut-away region 92 on the first half-shell of the insert. On either side of the anvil 130 are slot regions 140a and 140b, shown in the cross-section of FIG. 10, which house ejector springs 150a and 150b (not shown). Ejector springs 150a and 150b are, at their proximal end, attached to round side 104 and are flush with its outer circumference. However, the distal parts of the ejector springs 150a and 150b are biased such that, when unrestrained, the springs extend beyond the anvil 130 and enter the further recessed regions 94a and 94b of first half-shell 50. Alternatively, the cutaway region 92 may fully accommodate the ejector springs 150a and 150b without the need for recessed regions 94a and 94b. Spring 150b is shown in phantom line in FIG. 7.

With reference to FIG. 7 the recessed region 110 of the second half-shell has a slotted region 160 that houses stop spring 170. Stop spring 170 is secured nearby in a radial hole 171 in the second half-shell 100. Stop spring 170 is also biased such that, when unrestrained, it extends out beyond recessed area 110 through slotted region 200 in slide 120 and beyond joint diametrical planes of the inserts 50 and 100 to engage the fasteners.

Figure 3A:
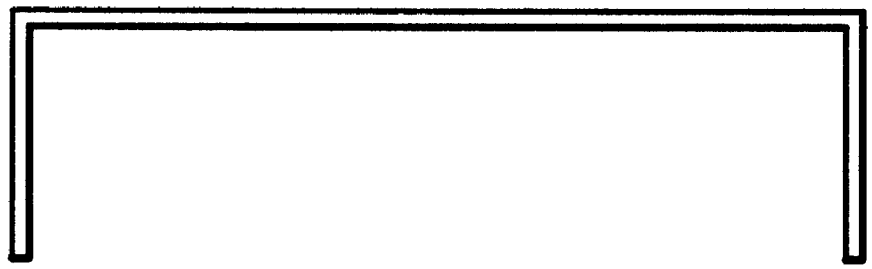
FIG. 3a is a schematic front view of a traditional U-shaped staple prior to application of a conventional shaping slide.
Figure 3B:
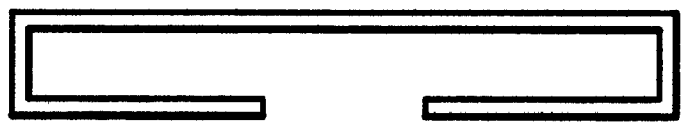
FIG. 3b is a schematic front view of a finished traditional U-shaped staple after application of a conventional shaping slide.
Figure 4A:
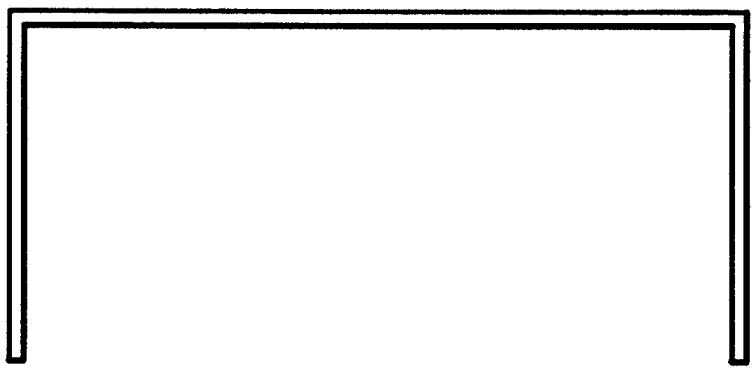
FIG. 4a is a schematic front view of an embodiment of the fastener of the present invention prior to application of the shaping slide.
Figure 4B:
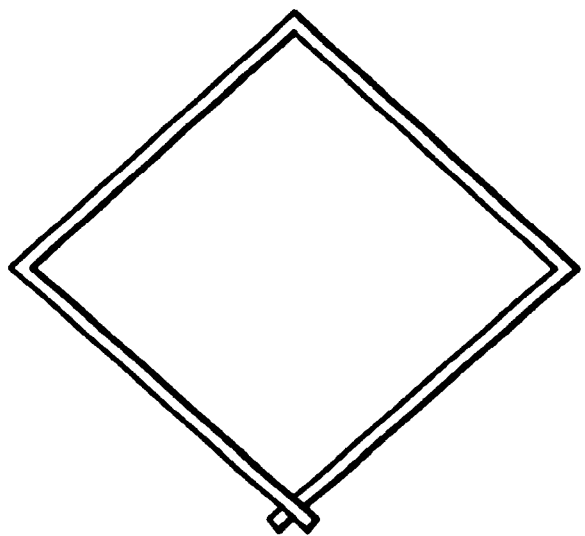
FIG. 4b is a schematic front view of an embodiment of the fastener of the present invention after application of an embodiment of the shaping slide of the present invention.
Figure 5A:
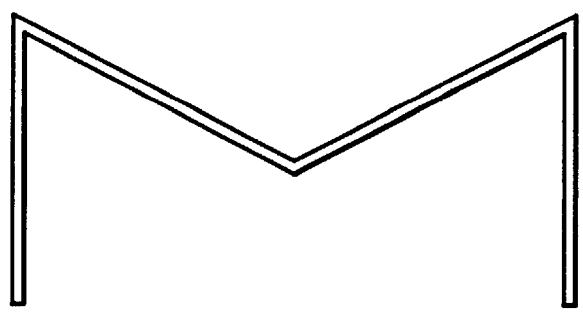
FIG. 5a is a schematic front view of alternate embodiment of the fastener of the present invention prior to application of an embodiment of the shaping slide of the present invention.
Figure 5B:
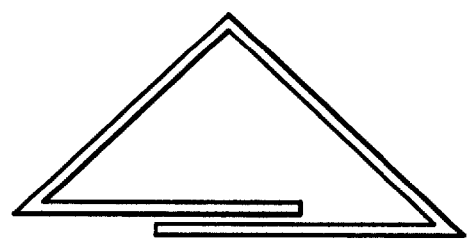
FIG. 5b is a schematic front view of the alternate embodiment of the fastener of the present invention after application of an embodiment of the shaping slide of the present invention.
Figure 5C:
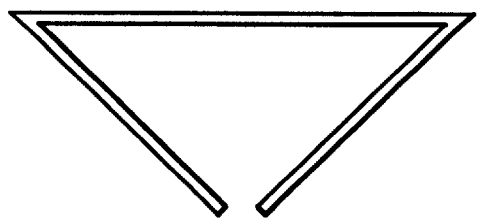
FIG. 5c is a schematic front view of an alternate embodiment of the fastener of the present invention, after application of an embodiment of the shaping slide of the present invention.
Figure 11:
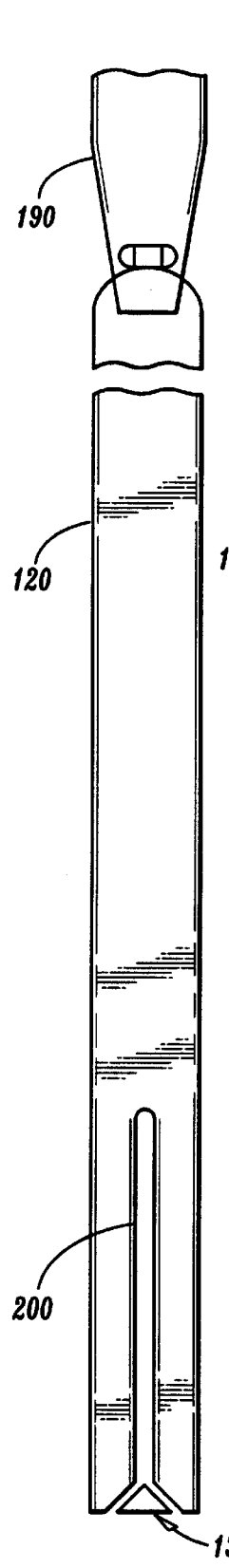
FIG. 11 is a front view of the slide, slide actuator and anvil rotated ninety-degrees from their depiction in FIGS. 7 and 8.

Slide 120, shown in detail in FIG. 11, along with slide actuator 190 are the only actuated parts in the preferred embodiment of the applicator 20. According to the preferred embodiment, slide 120 alternately restrains and releases all the biased moving parts of the applicator 20. Slide 120 is connected to slide actuator 190 within tube 40 at a point beyond the proximal end of both half-shells, 50 and 100. Alternatively, for an apparatus which does not have a detachable applicator, slide 120 may extend all the way into the handle portion, thus reducing the number of actuated parts in the applicator to one.

In the preferred embodiment slide 120 has a slotted region 200, which alternately restrains and releases stop spring 170 by allowing it to protrude through the slide. Slide 120 forms one wall of the storage channel created by the recessed region 70 in first half-shell 50.

The distal end of the slide 120, in the preferred embodiment, is forked and beveled to cooperate with triangular shaped anvil 130, as shown in FIGS. 11, 12a, 12b and 12c. This feature permits the slide width to be equal to or less than the fastener width. In the most preferred embodiment, the width of the slide 120, as well as that of the storage channel created by the surfaces of recessed region 70 and slide 120, extends almost the entire diameter of the joined half-shells, 50 and 100.

Figure 8:
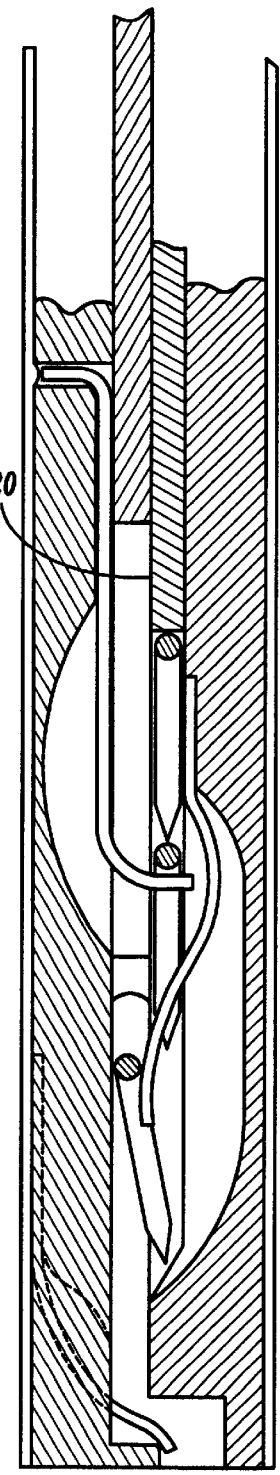
FIG. 8 is the same cross-section of the applicator of the embodiment of the surgical fastening tool shown in FIG. 7 but with the slide in the fully retracted position.

The preferred method of applying the fastener is demonstrated by FIGS. 7 and 8. FIG. 8 shows that when the slide 120 is fully retracted, the fastener positioning spring 60 urges the distal-most vertically-stacked fastener 80 from the storage channel to the driving channel located distal to slide 120. As the slide 120 is advanced in the driving channel by virtue of the slide actuator 190, the tines of the forked bottom of slide 120, shown in FIG. 12a, exert a downward pressure on the first fastener 80. As the slide 120 advances, it lifts the stop spring 170 out of slotted region 200 of the slide 120 (not shown), out of the storage channel where it previously restrained the second of the stacked fasteners and into recessed region 160 of the second half-shell piece 100. The second of the stacked fasteners is thereby released by stop spring 170 and advanced by the pusher 82 which is forward biased by pusher spring 84 (not shown in FIG. 8). The second fastener thus advances to the distal-most position in the storage channel, a position previously occupied by the first fastener.

As demonstrated by FIG. 7, advancement of the slide as described above also blocks fastener egress from the storage channel along its length, thereby preventing the next fastener from prematurely entering the driving channel. Additional advancement of the slide 120 pushes ejector springs 150a and 150b back into slotted regions 140a and 140b (not shown). This permits the foremost fastener to rest on the anvil 130 until the fully advanced slide shapes the fastener on the anvil, as demonstrated in FIGS. 7, 12a and 12b.

Once the fastener is formed on the anvil 130 and the toes of the fastener are securely in the tissue, the slide 120 is retracted such that biased ejector springs 150a and 150b are free to extend past the end of the anvil and kick the fastener off of the cantilevered anvil. As a result the applicator is freed and the fastener remains securely attached to the tissue and/or surgical material.

According to the preferred method, the slide 120 is subsequently retracted until the stop spring 170 passes through the slotted region 200 of the slide and hooks underneath a third fastener in the storage channel thereby preventing the third fastener's further advancement. Upon further retraction of the slide 120, the biased fastener positioning spring 60 is freed, thereby pushing the second fastener into the driving channel space vacated by slide 120.

Although the foregoing sequence of steps is preferred, in an alternate execution of the method, the sequence of steps triggered by the slide's action may involve simultaneous execution, or may even be reversed, as long as the method achieves the objectives of not permitting two fasteners into the driving channel at the same time, not permitting empty firing and not permitting the device to jam.

Figure 25:
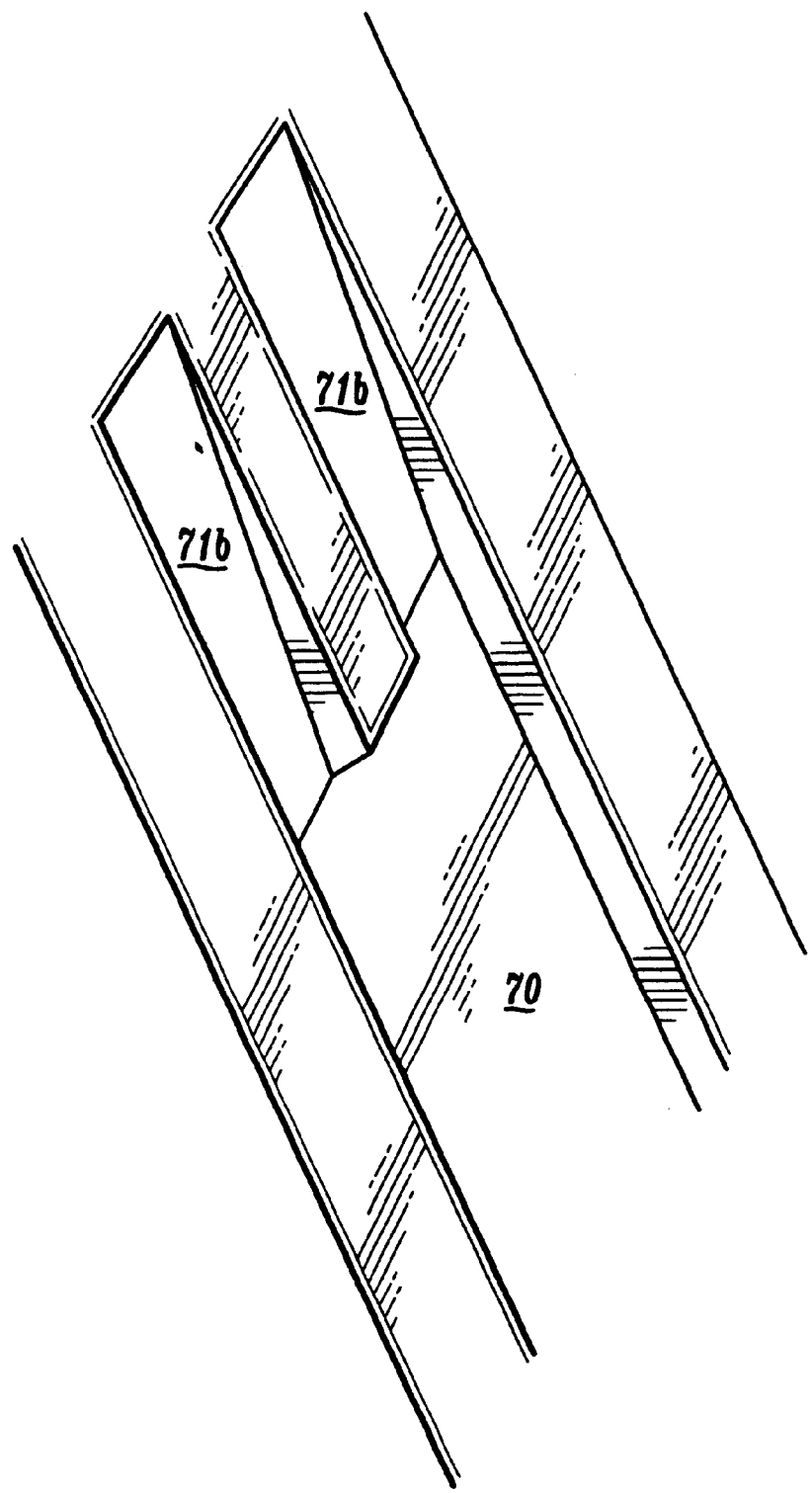
FIG. 25 is a three-dimensional perspective view of the storage channel of an alternative embodiment of the first half-shell of the fastener applicator.
Figure 26:
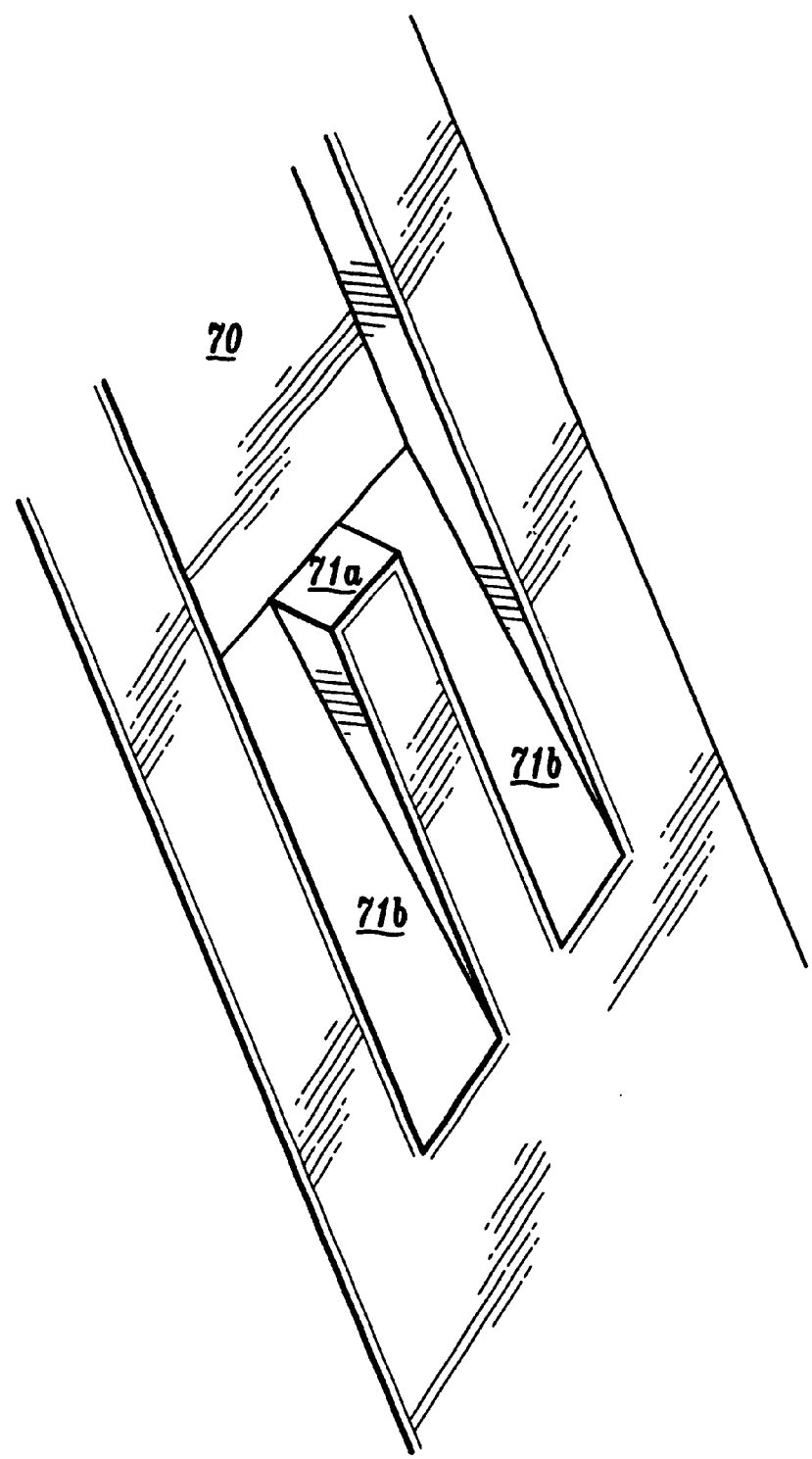
FIG. 26 is a three-dimensional perspective view of the storage channel of an alternative embodiment of the first half-shell of the fastener applicator.

In an alternative embodiment, the invention contemplates a mechanism for moving the distal-most fastener from the storage channel to the driving channel in a way that is not unduly dependent on the length of travel or size of the subsequent fastener in the storage channel. According to the alternative embodiment, the fastener 80 is moved out of the storage channel by virtue of a two-part ramp arising out of recessed region 70 of the storage channel, shown in FIGS. 24–26, said ramp comprising an interior section 71*a* and an exterior section 71*b*. As shown in FIG. 27, according to the alternative embodiment, as the distal-most fastener 80 moves forward along recessed region 70 by virtue of pusher 82 (not shown) and pusher spring 84 (not shown), the interior section of the ramp 71*a* transfers the back of the fastener 80 up into the driving channel. Because the interior section of the ramp 71*a* has a steeper angle than the exterior section of the ramp 71*b*, which is responsible for guiding the toes of the fastener into the driving channel, the back of the fastener 80 is brought into the driving channel while the toes remain in the interior section of the ramp within the storage channel. FIG. 27.

As shown in FIG. 27, as slide 120 moves forward, the toes, guided by ramp 71*b*, are brought into the driving channel by the forward force of the slide 120 against the back of the distal-most fastener 80 rather than by the forward force of the subsequent storage channel fastener being pushed forward in the storage channel by the pusher (not shown). The over-travel of the subsequent storage channel fastener prevents the distal-most fastener from falling back into the storage channel. The distal-most fastener is then driven out of the applicator as shown in FIG. 28. Although various angles of incline may achieve the principle taught herein, FIG. 29 shows the most preferred interior and exterior section angles of incline for the ramp, namely thirty percent incline for the interior section and nine percent incline for the exterior section.

According to the alternative embodiment, because the transfer mechanism only requires the back of the distal-most fastener to reach the driving channel, the subsequent fastener in the storage channel need not travel forward as great of distance or be as great of length to move the distal-most fastener fully into the driving channel. Thus, by reducing the need for extended forward positioning of the subsequent fastener in the storage channel, the fastener applicator may store and use fasteners of shorter toe lengths. The alternative embodiment also reduces the sensitivity of the transfer mechanism by reducing the reliance on precision in the forward positioning of the subsequent storage channel fastener. Moreover, the alternative embodiment eliminates the fastener positioning spring 60 (depicted in FIGS. 7 and 8) thereby simplifying the overall fastener mechanism and eliminating any concern for precise spacing and fastener length created by engagement of the fastener with the fastener positioning spring.

Figure 13:
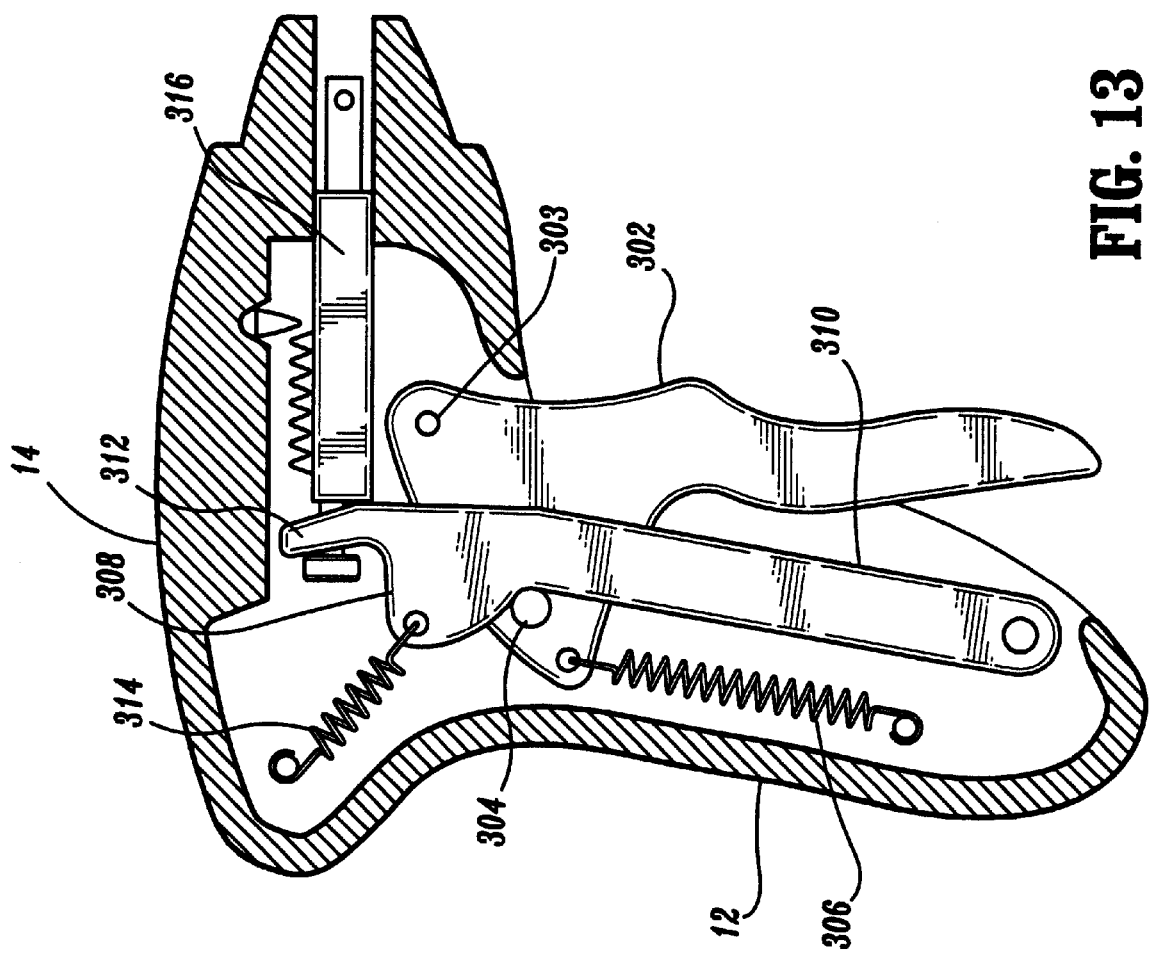
FIG. 13 is a cross-sectional view of the handle portion and trigger portion of a preferred embodiment of the surgical fastening tool.
Figure 14:
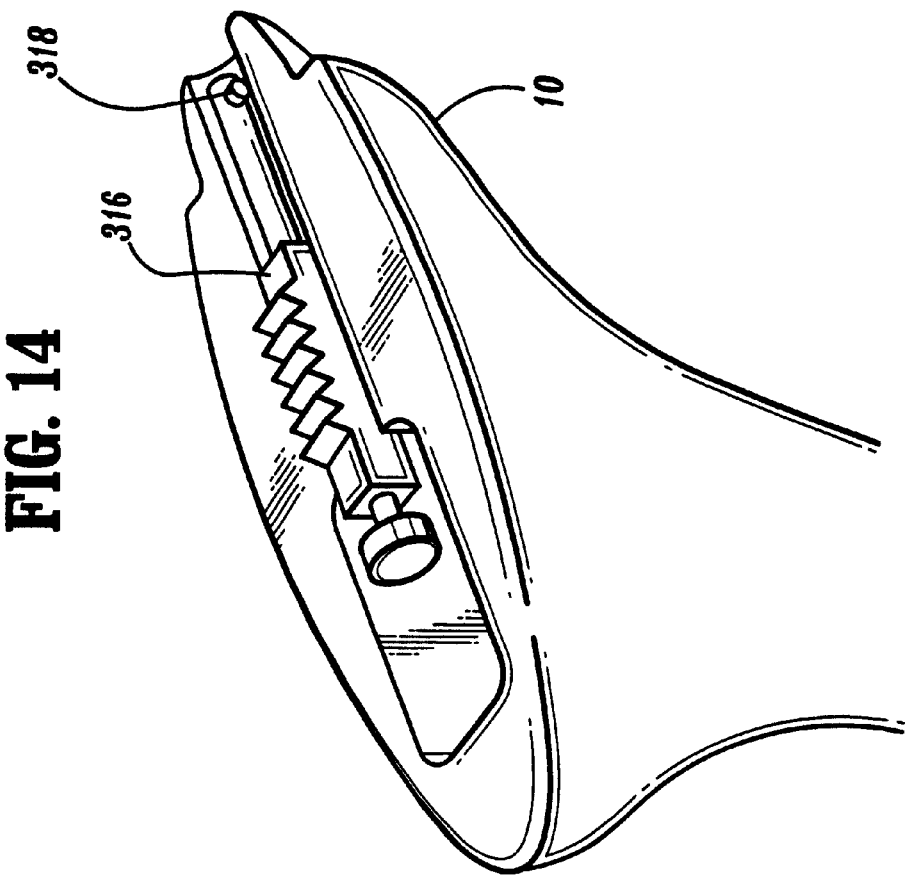
FIG. 14 is a three-dimensional cross-sectional perspective view of a preferred embodiment of the fastening tool wherein the applicator is readily detachable from the body portion.

With respect to the handle portion 10 and the trigger portion 30, the invention contemplates that there are many ways to fashion these elements. However, to further the goals of minimal jamming and misfiring by the miniaturized tool, the invention teaches a preferred handle portion and trigger portion, shown separately in FIG. 13, that work consistently and reliably with the preferred applicator embodiment and other applicator designs. In a preferred embodiment, the handle portion 10 consists of a pistol grip portion 12 and a barrel portion 14. The trigger portion 30 of the preferred embodiment comprises a trigger 302 having a cam follower 304 which fits within the handle portion 10 and is pivotally attached at pivot 303 to the pistol grip portion 12 and biased by spring 306. The cam follower 304 engages a cam 308 which extends from a cooperating hinged lever 310 that resides within the pistol grip portion 12. The hinged lever 310 is pivotally attached near the butt of the pistol grip portion 12 and extends through the handle portion 10 into the barrel portion 14. The hinged lever 310 has at its upper end a fork 312 whose crotch is aligned with the axis of the tubular housing 40 of applicator 20 (not shown). The fork 312 is biased away from the applicator 20 (not shown) by fork biasing spring 314. The fork 312 connects to a plunger/ratchet assembly 316 which has a distal and proximal end. The proximal end of plunger/ratchet assembly 316 is grooved to accept the fork 312. As shown in FIG. 14, the distal end of plunger/ratchet assembly 316 connects to slide actuator 190 which in turn connects to slide 120 (not shown) within the applicator 20. The trigger portion 30 is contained in a recess of handle portion 10 which may consist of two halves fitted together, such as 10*a* and 10*b*.

The preferred embodiment functions as follows: squeezing trigger 302 causes lever fork 312 to be thrust toward the distal end of the barrel portion 14 by the response of the cam 308 to action of the cam follower 304. Release of the trigger 302 causes fork 312 to retract to its original position by virtue of a fork biasing spring 314 and trigger biasing spring 306 which returns these same elements back to their resting positions.

The limited number of fasteners deployable within a miniaturized device may create the need for easy, reliable reloading during extensive surgical procedures. Many hospitals desire to have a reusable portion of the fastener applicator tool. FIG. 14 shows a preferred embodiment in which an applicator 20 containing stacked fasteners 80 (not shown) that is readily detachable from body portion 10 by rotating the applicator 20 and axially moving it away from the handle portion 10. A new applicator is readily attached in the reverse manner. The applicator 20 thus functions as a fastener magazine and is replaced every time a new supply of fasteners is required.

In the preferred embodiment of this aspect of the invention, slide actuator 190 is notched at its proximal end to accept the drive pin 318 present on the distal end of the plunger/ratchet assembly 316. However, because the slide actuator 190 would otherwise freely move within applicator 20 when the applicator 20 is not attached to the handle portion 10, the slide actuator 190 is locked into place by virtue of an "L"-shaped pin 320 having a flat spot on its shank.

Figure 15A:
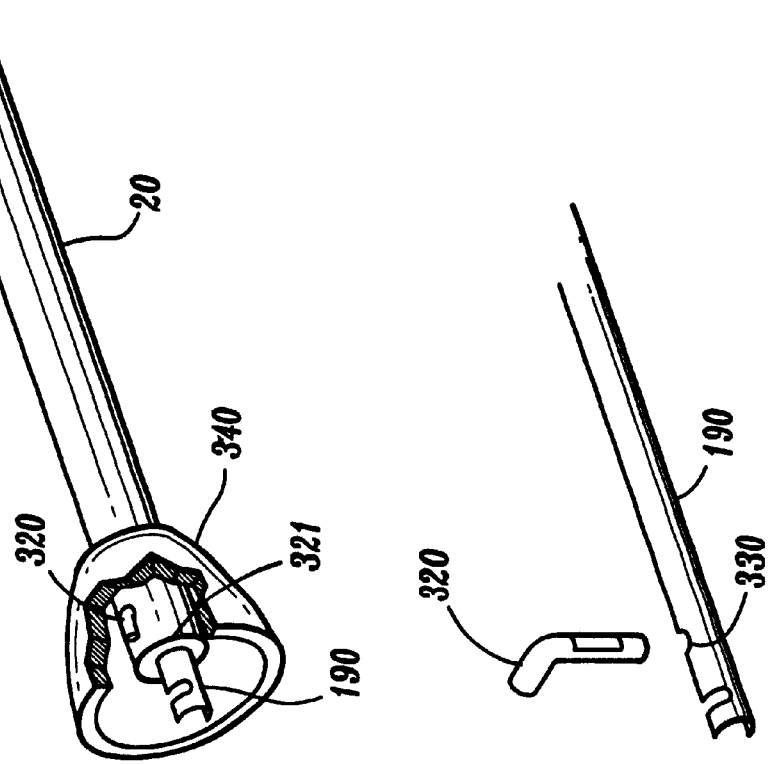
FIG. 15a is a three-dimensional perspective view of the proximal end of the slide actuator and "L"-shaped pin with the pin in the unlocked position.

FIG. 15*a* illustrates a simplified close-up of this locking feature. The leg of "L"-shaped pin 320 passes through hub 321 (not shown) and engages a notched region 330 of slide actuator 190. When the leg portion of "L"-shaped pin 320 is parallel to the bore of the tubular housing 40, as in FIG. 14, the shank engages notched region 330 of the slide actuator 190 and the slide actuator is locked. However, when the external portion of pin 320 is transverse to the bore of the tubular housing 40, as in FIG. 15*a*, the flat portion of the pin shank is free of notches 330 and as a result the actuator 190 is free to slide axially in response to actuation by the handle and trigger portions. As shown in FIG. 14, the pin 320 and the proximal end of the slide actuator 190 are preferably protected by a skirt 340 to prevent any inadvertent change in the position of the "L" shaped shaped pin 320 during handling of the actuator. The skirt 340 also protects against damage to the proximal end of the slide actuator 190. According to this feature, the distal end of the barrel portion 14 of handle portion 10 of the fastener applicator tool is received within the skirt 340 and connected to the slide actuator 190 within the skirt.

With reference to FIG. 14, which shows detail of the applicator magazine attachment to the handle portion, the handle portion 10 is made of two body portions, 10a and 10b, which fit together, house the trigger 302, fork lever 312 and plunger/ratchet assembly 316. According to this applicator magazine embodiment, the handle portion 10 comprises a socket at its distal end that is shaped to receive the proximal end hub 321 of applicator 20. The plunger/ratchet assembly 316 is fitted with a drive pin 318 for engagement with slide actuator 190 and the proximal end of the slide actuator 190 is notched to receive the drive pin 318. In lieu of a skirt 340, applicator 20 may simply have a grip disposed about its circumference that allows the user to grip the applicator 20 during assembly with the handle portion 10.

Figure 15B:
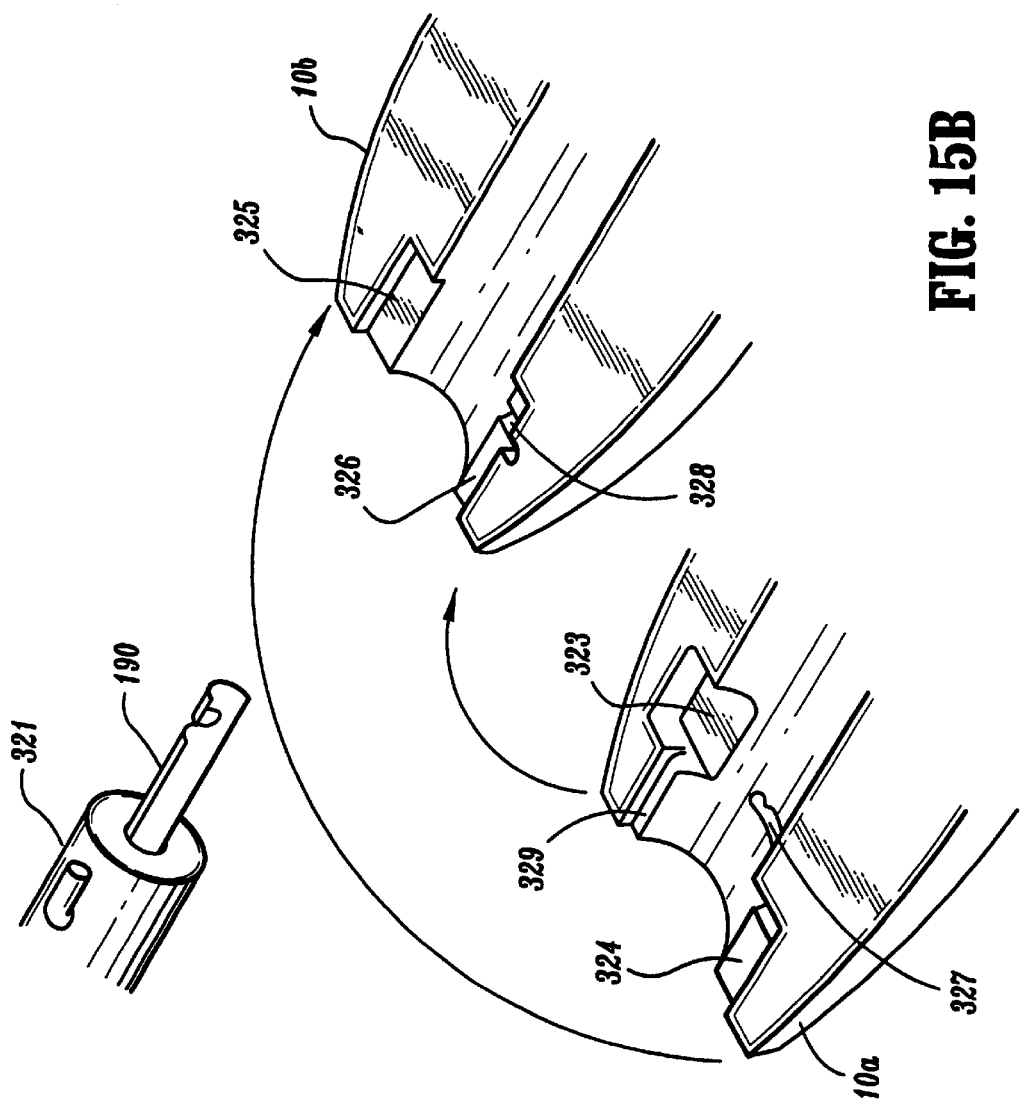
FIG. 15b is an exploded view of the handle portion revealing the cam surfaces and recessed regions which provide the mechanism for attaching the applicator to the handle portion as well as the slide actuator lock and release mechanism.

In the preferred applicator magazine attachment mechanism shown in FIG. 15b, the applicator 20 is inserted into the handle portion 10, comprised of two handle halves 10a and 10b, by sliding its proximal end into the socket of the handle portion 10, and rotating the applicator. The act of inserting the proximal end of the applicator 20 into the distal end of the handle portion 10 and rotating it serves several purposes: first, it locks the applicator 20 onto the handle body 10; second, the rotation causes the "L"-shaped pin 320 to rotate in response to a cam surface 328 thereby freeing the slide actuator 190 from its locked position into a ready position; third, rotation causes the notch in the slide actuator 190 to engage the drive pin 318 on the plunger/ratchet assembly 316; and fourth, detent structure 327 engages the shank of the "L"-shaped pin, preventing inadvertent rotation in use. FIG. 15b shows the detail of the mechanism for connecting the applicator to the handle. The two handle halves 10a and 10b comprising relief grooves 323, 324, 325 and 326 and cam surfaces 328 and 329, engage the proximal end of the actuator hub 321 for the purpose of releasably holding the applicator to the assembled handle. In FIG. 15b, the handle halves are shown separated and opened out in juxtaposition to illustrate their features. Also shown is the actuator hub 321 with slide actuator 190 locked in place by the "L"-shaped pin. The embodiment shown here does not incorporate a skirt as in FIG. 14. On insertion of the hub into the handle bore that is created by the junction of handle halves 10a and 10b, the relief grooves 323, 324, 325 and 326 form grooves of different depths such that the hub may only be assembled in one position because of the profile of the "L"-shaped pin 320. After full insertion, clockwise rotation presses the arm of the "L"-shaped pin against cam surface 328 and turns the arm 90° to the axis of the hub 321. Rotation is continued until the shank of the "L"-shaped pin passes past the detent 327 at the end of the groove in the handle to lock the actuator in position. The actuator is thus locked in place ready for use, and cannot inadvertently back-rotate and uncouple. After insertion, the device is ready for operation as if it were a tool of unitary construction. Reversing this rotation step frees the slide actuator 190 from drive pin 318, and on withdrawal, cam 329 rotates the leg of the "L"-shape pin back into engagement with the notched region of the slide actuator 190 on withdrawal, thereby locking the actuator, and disconnects the applicator 20 from the handle portion 10. If a skirt is incorporated into this attachment apparatus as in FIG. 14, it may be integral with or attached to the hub 321. If the apparatus is of unitary construction, the releasable attachment mechanism may be eliminated and the cooperating elements are non-detachably joined.

Figure 17:
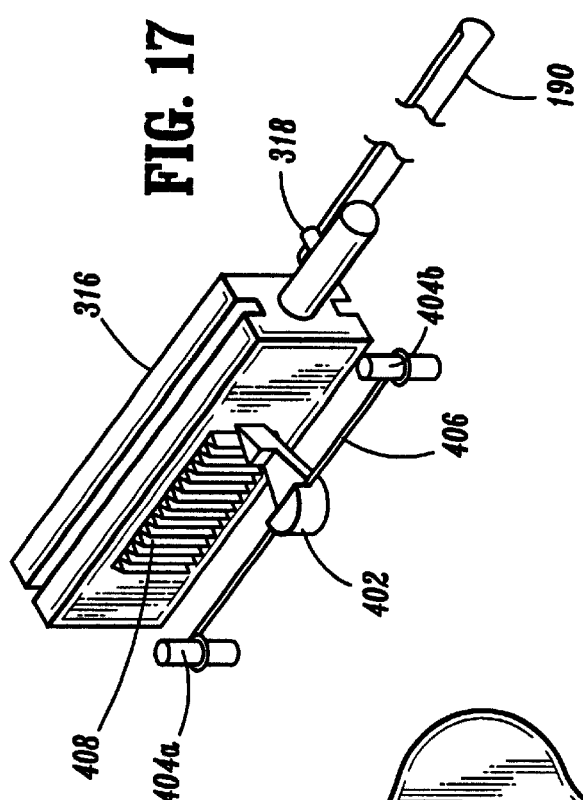
FIG. 17 is a three-dimensional rendering of the preferred plunger assembly of the present invention showing a pawl standing clear of the ratchet portion of the plunger assembly following completion of a stroke.
Figure 16:
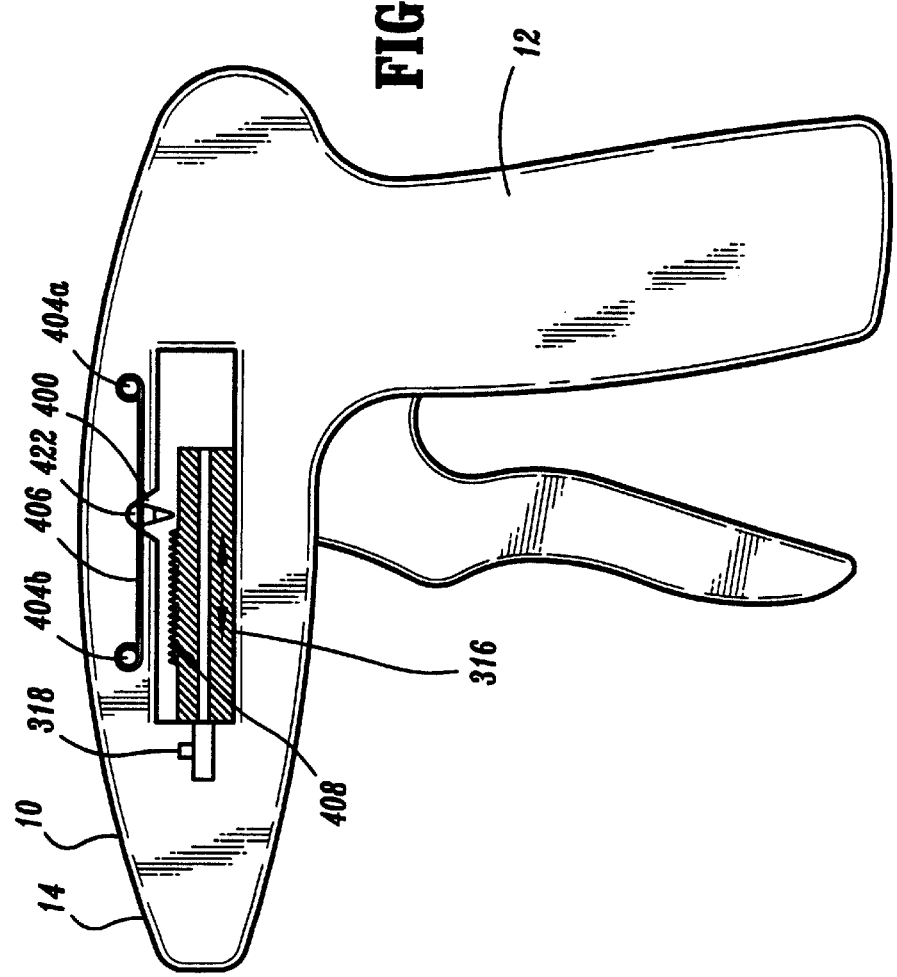
FIG. 16 is a cross-section of the preferred handle portion of the present invention wherein the handle portion contains a tapered slot that houses a pawl.

According to another aspect of the invention, the preferred embodiment includes a ratchet and pawl system designed to guarantee complete, irreversible travel of the applicator mechanism during each stroke of the application cycle. This aspect of the invention, shown in FIGS. 16 and 17, contemplates that the plunger/ratchet assembly 316 reciprocates backward and forward within the barrel portion 14 of the handle portion 10. A tapered slot 400 is provided in the handle portion 10 and a pawl 402 is placed within that tapered slot. A wire pawl spring 406 extends between posts 404a and 404b. The pawl spring 406 urges the pawl 402 into a perpendicular position relative to the direction of plunger travel by means of a slot in the pawl. The side of the plunger/ratchet assembly 316 that faces pawl 402 has a series of grooves forming a ratchet 408 which extends approximately as far as the extent of travel of the plunger/ratchet assembly 316 within the handle portion 10. The length of pawl 402 is somewhat greater than the distance between the bottom of the tapered groove and the bottom of the ratchet grooves. The pawl 402 is thus trapped at an oblique angle between the slot 400 and the ratchet 408 during plunger travel.

Figure 18:
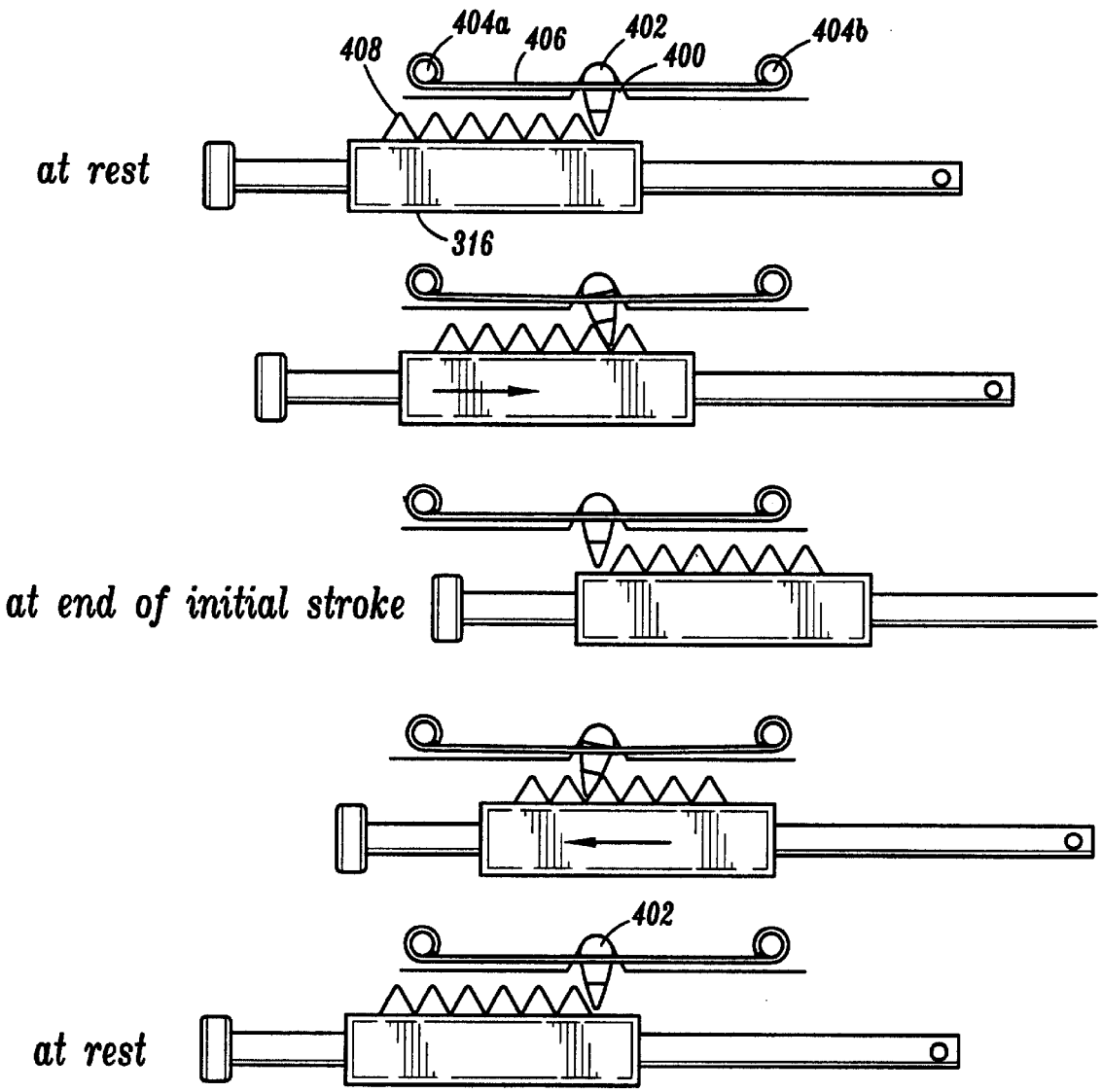
FIG. 18 is a time-sequenced frontal view of the plunger and pawl mechanism undergoing one complete cycle of application and retraction.
Figure 19:
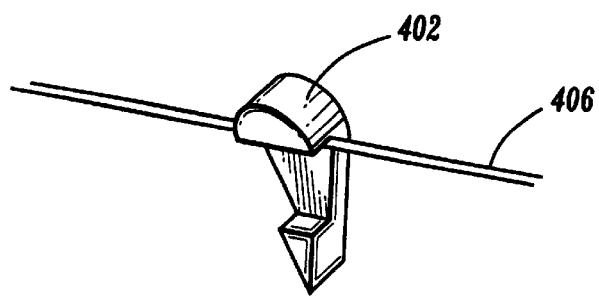
FIG. 19 is a three-dimensional perspective view of the pawl and wire spring.
Figure 20A:
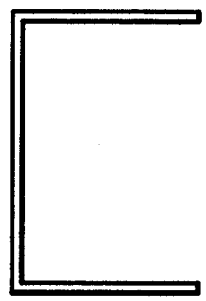
FIG. 20a is a schematic front view of an embodiment of the fastener of the present invention prior to application of the shaping slide and double anvil of FIG. 22.
Figure 20B:
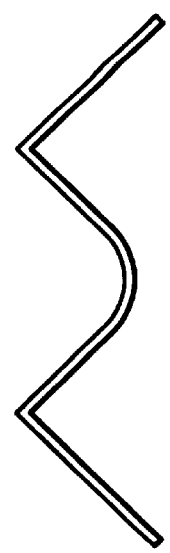
FIG. 20b is a schematic front view of an embodiment of the fastener of the present invention after the application of the shaping slide and double anvil of FIG. 22.
Figure 21A:
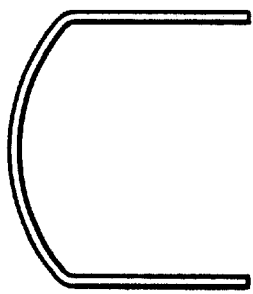
FIG. 21a is a schematic front view of an embodiment of the fastener of the present invention prior to application of the shaping slide and double anvil as shown in FIG. 23.
Figure 21B:
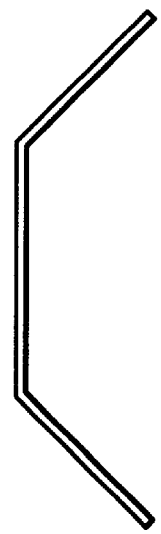
FIG. 21b is a schematic front view of an alternate embodiment of the fastener of the present invention after the application of the shaping slide as shown in FIG. 23.
Figure 22:
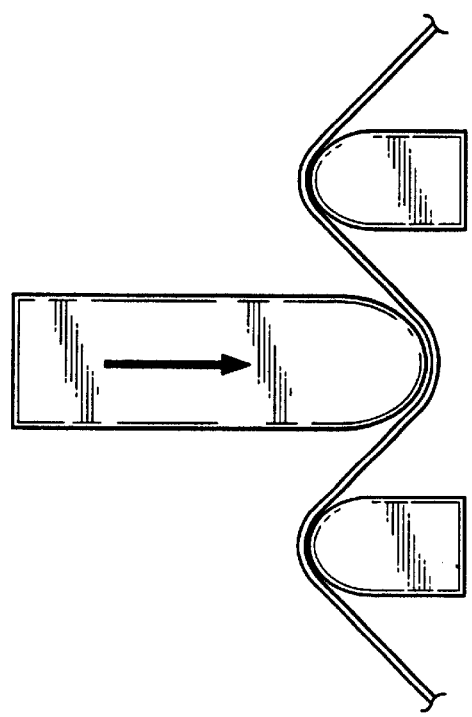
FIG. 22 shows an alternate slide/anvil combination which will maximize finished span as shown in FIG. 20b.
Figure 23:
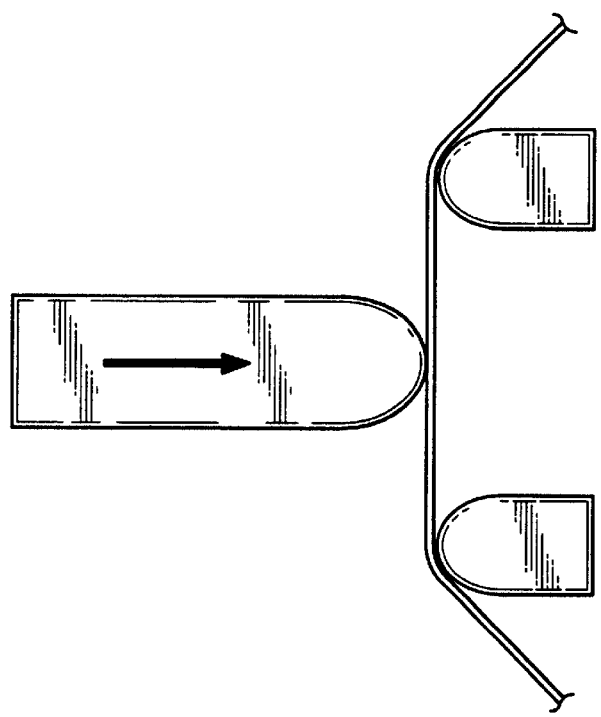
FIG. 23 shows an alternate slide/anvil combination which, with reduced travel of the slide relative to that shown in FIG. 22, will maximize finished span as shown in FIG. 21b.

FIG. 18 shows the complete fastener application cycle with reference to the plunger/ratchet assembly 316. Once the plunger travel is initiated and the pawl is engaged in the ratchet, any attempt to reverse direction causes the pawl 402 to jam between the slot 400 and the ratchet 408 thereby immediately stopping counter-travel. The plunger/ratchet assembly thus can only move in the initial stroke direction until the pawl travels past the end of the ratchet 408 and out of engagement with the plunger/ratchet assembly. At that point, the wire pawl spring 406 causes the pawl 402 to assume a position that is perpendicular to the ratchet 408. The initiation of travel of the plunger/ratchet assembly in the opposite direction (the return stroke) again places the pawl 402 into engagement with the ratchet at an angle, but this time the pawl is oriented in the opposite sense. Thus, the pawl's orientation makes mid-stroke reversal impossible once again until travel is complete and the pawl clears the other end of the ratchet completing the cycle. By adjusting the geometry of the ratchet and pawl as well as providing travel stops for the plunger assembly, the device eliminates mid-stroke reversals and thereby helps prevent jamming, non-firing and misfiring. FIG. 19 shows in detail the spring 406 deployed in the slot of the pawl 402 so as to orient the pawl.

While particular endoscopic devices and methods have been described for applying fasteners, once this description is known, it will be apparent to those of ordinary skill in the art that other embodiments and alternative steps are also possible without departing from the spirit and scope of the invention. Moreover, it will be apparent that certain features of each embodiment can be used in combination with devices illustrated in other embodiments. For example, the four various aspects of the invention may be mixed and matched to create a variety of surgical fastening devices with varying features. Accordingly, the above description should be construed as illustrative, and not in a limiting sense, the scope of the invention being defined by the following claims.

What is claimed is:

1. A fastening apparatus for use in endoscopic surgery comprising:

a handle portion;

a triggering mechanism operatively connected to the handle portion;

a plurality of vertically stacked fasteners;

at least one ramp for guiding toes of each of the plurality of vertically stacked fasteners into a driving channel; and a fastener applicator connected to the handle portion, the fastener applicator comprising a shaping slide and at least two anvils.

2. The apparatus of claim 1 wherein at least one of said anvils has an essentially half-circular cross-section.

3. The fastening apparatus for use in endoscopic surgery as recited in claim 1, wherein the fastener applicator defines a longitudinal channel for storing the plurality of fasteners.

4. A fastening apparatus for use in endoscopic surgery comprising:

a handle portion;

a triggering mechanism positioned at least partially within the handle portion;

a plurality of vertically stacked fasteners;

at least one ramp for guiding toes of each of the plurality of vertically stacked fasteners into a driving channel; and a fastener applicator connected to the handle portion, the fastener applicator comprising an anvil, said anvil having a top, and a shaping slide, wherein said shaping slide, when fully extended, does not extend beyond the top of said anvil.

5. The fastening apparatus for use in endoscopic surgery as recited in claim 4, wherein the fastener applicator defines a longitudinal channel for storing the plurality of fasteners.

* * * * *